(12) United States Patent
Kazmierski et al.

(10) Patent No.: US 10,239,894 B2
(45) Date of Patent: Mar. 26, 2019

(54) INHIBITORS OF INDOLEAMINE 2,3-DIOXYGENASE

(71) Applicant: GLAXOSMITHKLINE INTELLECTUAL PROPERTY DEVELOPMENT LIMITED, Brentford, Middlesex (GB)

(72) Inventors: Wieslaw Mieczyslaw Kazmierski, Research Triangle Park, NC (US); Martha Alicia De La Rosa, Research Triangle Park, NC (US); Vicente Samano, Research Triangle Park, NC (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/578,861

(22) PCT Filed: Jun. 30, 2016

(86) PCT No.: PCT/IB2016/053947
§ 371 (c)(1),
(2) Date: Dec. 1, 2017

(87) PCT Pub. No.: WO2017/002078
PCT Pub. Date: Jan. 5, 2017

(65) Prior Publication Data
US 2018/0298035 A1    Oct. 18, 2018

Related U.S. Application Data

(60) Provisional application No. 62/187,937, filed on Jul. 2, 2015.

(51) Int. Cl.
*C07F 5/02* (2006.01)
*A61P 37/06* (2006.01)

(52) U.S. Cl.
CPC .............. *C07F 5/025* (2013.01); *A61P 37/06* (2018.01)

(58) Field of Classification Search
CPC ....................................................... C07F 5/025
See application file for complete search history.

(56) References Cited

FOREIGN PATENT DOCUMENTS

| WO | WO 2006/122150 A1 | 11/2006 |
| WO | WO 2010/005958 A2 | 1/2010 |
| WO | WO 2014/066834 A1 | 5/2014 |

OTHER PUBLICATIONS

Potola et al. Blood. Oct. 1, 2005; 106(7): 2382-2390 (Year: 2005).*

* cited by examiner

*Primary Examiner* — Emily A Bernhardt
(74) *Attorney, Agent, or Firm* — Robert H. Brink; Kathryn A. Lutomski; Edward R. Gimmi

(57) ABSTRACT

Provided are compounds of formula (I) and pharmaceutically acceptable salts thereof, their pharmaceutical compositions, their methods of preparation, and methods for their use in the prevention and/or treatment of HIV; including the prevention of the progression of AIDS and general immunosuppression.

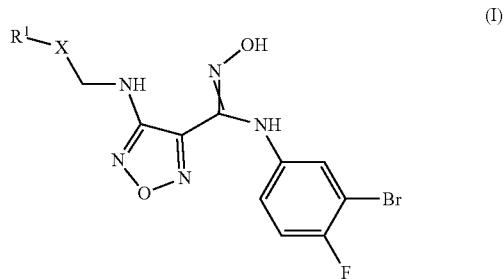

7 Claims, 1 Drawing Sheet

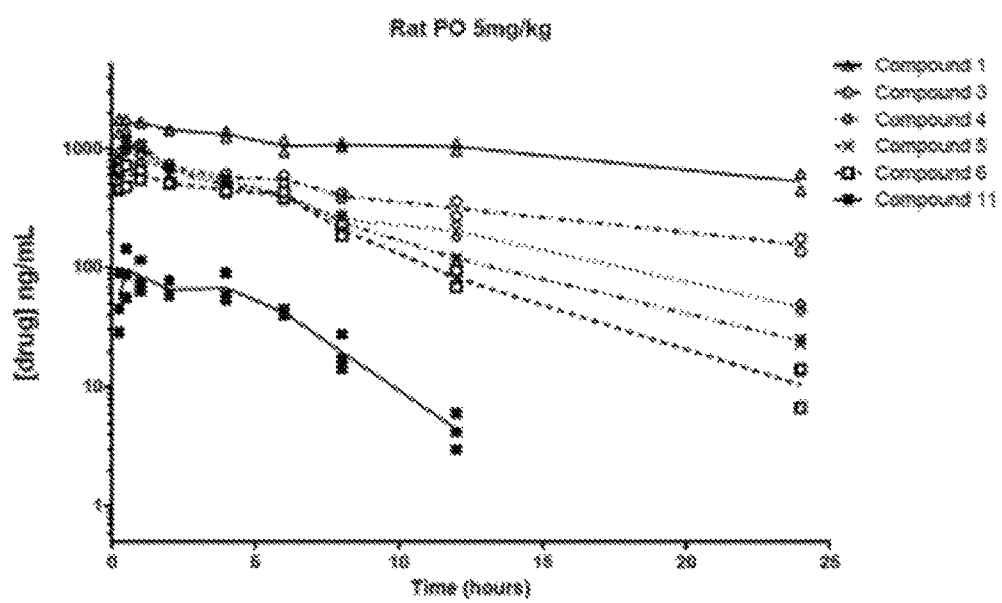

INHIBITORS OF INDOLEAMINE 2,3-DIOXYGENASE

This application is a § 371 of International Application No. PCT/IB2016/053947, filed 30 Jun. 2016, which claims the benefit of U.S. Provisional Application No. 62/187,937, filed 02 Jul. 2015.

FIELD OF THE INVENTION

Compounds, methods and pharmaceutical compositions for the prevention and/or treatment of HIV; including the prevention of the progression of AIDS and general immunosuppression, by administering certain indoleamine 2,3-dioxygenase inhibitor compounds in therapeutically effective amounts are disclosed. Methods for preparing such compounds and methods of using the compounds and pharmaceutical compositions thereof are also disclosed.

BACKGROUND OF THE INVENTION

Human immunodeficiency virus type 1 (HIV-1) leads to the contraction of acquired immune deficiency disease (AIDS). The number of cases of HIV continues to rise, and currently over twenty-five million individuals worldwide suffer from the virus. Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still required due to a number of issues including but not limited to undesirable drug-drug interactions; drug-food interactions; non-adherence to therapy; drug resistance due to mutation of the enzyme target; and inflammation related to the immunologic damage caused by the HIV infection.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur and the survival and quality of life are not normalized as compared to uninfected persons. Indeed, the incidence of several non-AIDS morbidities and mortalities, such as cardiovascular disease, frailty, and neurocognitive impairment, are increased in HAART-suppressed, HIV-infected subjects. This increased incidence of non-AIDS morbidity/mortality occurs in the context of, and is potentially caused by, elevated systemic inflammation related to the immunologic damage caused by HIV infection.

Sustained successful treatment of the HIV-1-infected patient population with drugs will therefore require the continued development of new and improved drugs with new targets and mechanisms of action including antiretroviral and/or interventions aimed at restoration of the immune system and decreasing the systemic inflammation.

IDO is a monomeric 45 kDa extrahepatic heme-containing dioxygenase which catalyzes the oxidative pyrrole ring cleavage reaction of l-Trp to N-formylkynurenine utilizing molecular oxygen or reactive oxygen species via three proposed reaction mechanisms. IDO is an enzyme that is the rate limiting step in the kynurenine pathway of tryptophan catabolism. IDO catalyzes the dioxidation of the indole ring of tryptophan (Trp), producing N-formyl-lynurenine (NFK), which is then metabolized by other enzymes into several downstream metabolites such as kynurenine (Kyn) and 3-hydroxy-anthranilate (HAA). The depletion of Trp and accumulation of Kyn and HAA have immunomodulatory activity, typically exemplified by decreased T cell activation and proliferation, enrichment of regulatory CD4+ T cells, and depletion of IL-17-producing CD4+ T cells. IDO activity therefore has a general immunosuppressive impact.

IDO is expressed in response to inflammation and is considered an important counter balance to prevent collateral tissue damaged during prolonged inflammation. IDO expression and activity are elevated during chronic viral infections such as HIV and HCV, chronic bacterial infections, as well as acute conditions such as sepsis. The IDO-mediated shift of Th17 to Treg differentiation of helper T cells likely plays a role in the intestinal immune dysfunction during HIV infection, likely related to the observed elevated systemic inflammation and increased incidence of non-AIDS morbilidty/mortality. In addition, IDO activity likely also plays a role in the persistence of pathogens and cancer, and inhibition of IDO may improve clearance mechanism, potentially leading to cure of these chronic diseases. IDO may also play a role in neurological or neuropsychiatric diseases or disorders such as depression by modulating serotonin synthesis or production of excitatory neurotoxins such as kynurenine. As such, pharmacologic inhibition of IDO has application in a broad range of applications from neurology, oncology, and infectious diseases.

It would therefore be an advance in the art to discover IDO inhibitors that effectively balance of the aforementioned properties as a disease modifying therapy in HIV infections to decrease the incidence of non-AIDS morbidity/mortality; and/or an immunotherapy to enhance the immune response to HIV, HBV, HCV and other viral infections, bacterial infections, fungal infections, and to tumors; and/or for the treatment of depression or other neurological/neuropsychiatric disorders.

SUMMARY OF THE INVENTION

The present invention provides compounds which are modulators of IDO having Formula (I):

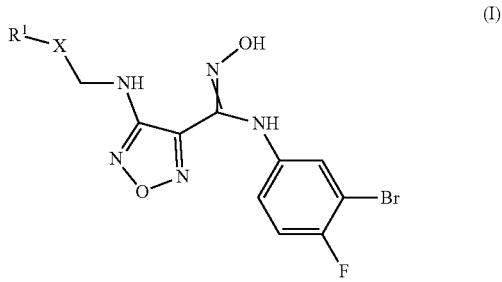

or pharmaceutically acceptable salt, thereof, wherein:

X is $CH_2$ or $C(O)$;

$R^1$ is $-NR^2R^3$;

$R^2$ is $-H$ or $-CH_3$;

$R^3$ is selected from the group consisting of:

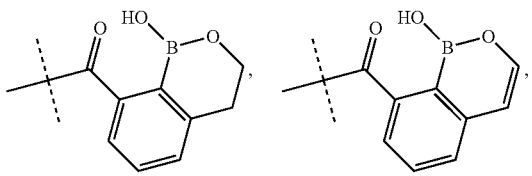

-continued

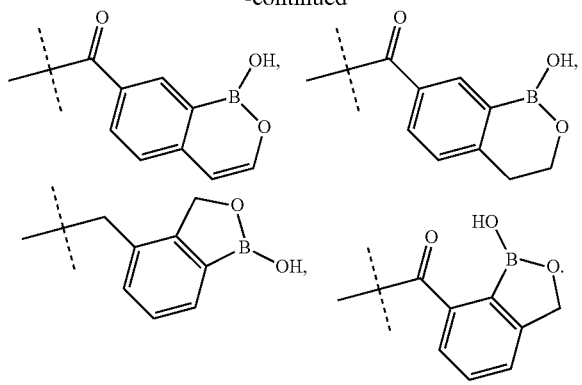

The present invention further provides compositions comprising a compound of the invention, or pharmaceutically acceptable salt thereof, and at least one pharmaceutically acceptable carrier.

In some embodiments, the compounds of the invention have Formula (II):

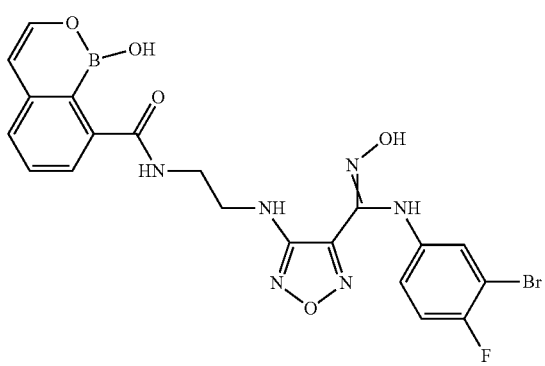

(II)

or pharmaceutically acceptable salt, thereof.

In some embodiments, the compounds of the invention have Formula (III):

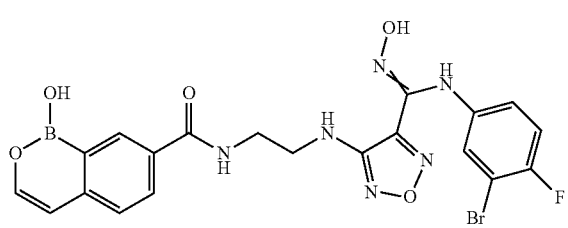

(III)

or pharmaceutically acceptable salt, thereof.

In some embodiments, the compounds of the invention have Formula IV):

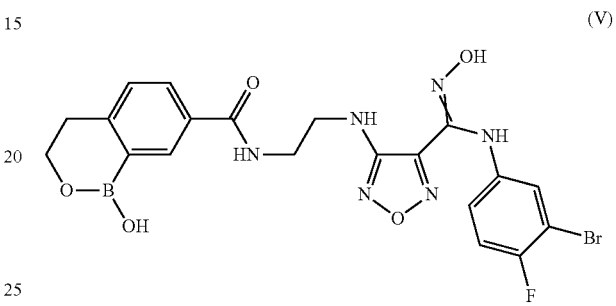

(IV)

or pharmaceutically acceptable salt, thereof.

In some embodiments, the compounds of the invention have Formula (V):

(V)

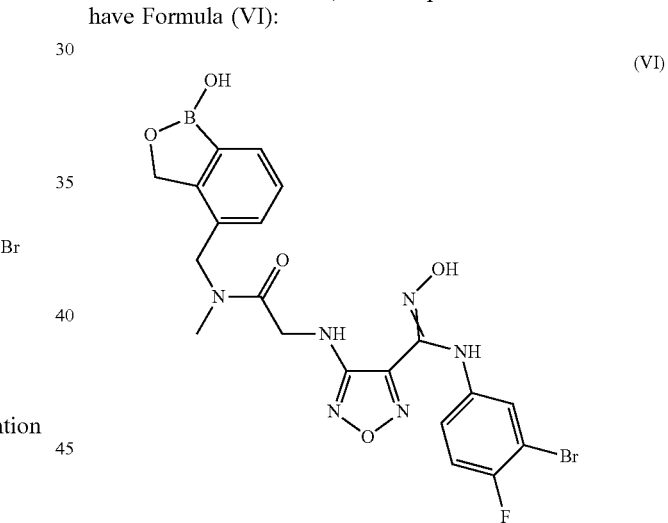

or pharmaceutically acceptable salt, thereof.

In some embodiments, the compounds of the invention have Formula (VI):

(VI)

or pharmaceutically acceptable salt, thereof.

In some embodiments, the compounds of the invention have Formula (VII):

(VII)

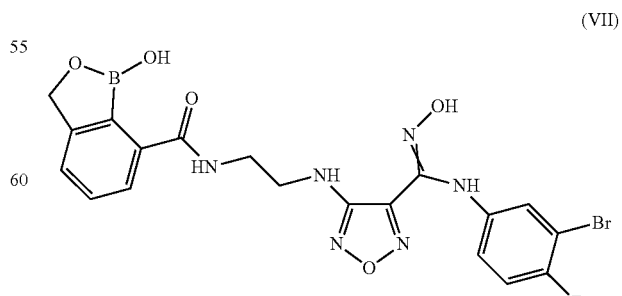

or pharmaceutically acceptable salt, thereof.

BRIEF DESCRIPTION OF THE DRAWINGS

FIG. 1 shows Rat Oral Pharmacokinetic (PK), Drug concentration (ng/m L) vs. Time (hours)

DETAILED DESCRIPTION OF REPRESENTATIVE EMBODIMENTS

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or ACN are preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes isomers, or mixed isomers, which by definition are the molecules of identical atomic compositions, but with different bonding arrangements of atoms or orientations of their atoms in space i.e., isomers are two or more different substances with the same molecular formula. Cis and trans geometic isomers of the compound of the present invention are described and may be isolated as a mixture of isomers or as separated isomeric forms. A bond in a structure diagram represented by a wavy line "〜" or a crossed line "⧖" is intended to indicate that the structure represents the cis or the trans isomer, or a mixture of the cis and trans isomer in any proportion. Isomerism, in the field of clinical pharmacology and pharmacotherapeutics, can differ in their pharmacokinetic and pharmacodynamic which may provide introducing safer and more effective drug alternatives of newer as well as existing drugs.

In accordance with one embodiment of the present invention, there is provided a compound having the structure of Formula (I):

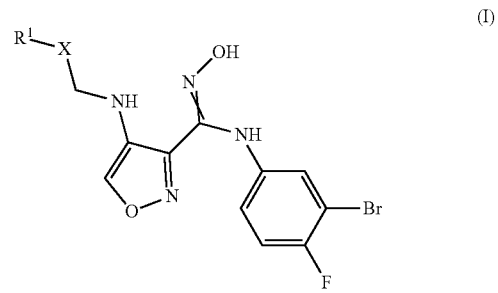

or pharmaceutically acceptable salt, thereof, wherein:
X is $CH_2$ or $C(O)$;
$R^1$ is $—NR^2R^3$;
$R^2$ is $—H$ or $—CH_3$;
$R^3$ is selected from the group consisting of:

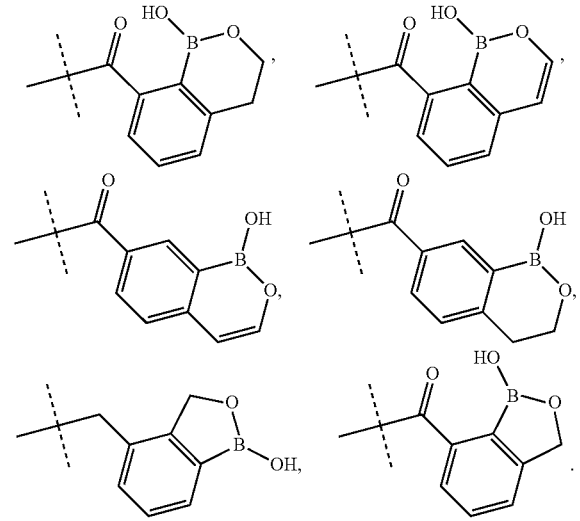

The present invention further provides compositions comprising a compound of the invention, or pharmaceutically acceptable salt thereof, and at least one pharmaceutically acceptable carrier.

The present invention further provides methods of modulating activity of indoleamine 2,3-dioxygenase by contacting the indoleamine 2,3-dioxygenase with a compound of the invention, or pharmaceutically acceptable salt thereof.

The present invention further provides methods for the prevention and/or treatment of HIV; including the prevention of the progression of AIDS and general immunosuppression in a patient by administering to the patient an effective amount of a compound of the invention, or pharmaceutically acceptable salt thereof.

The present invention further provides methods of treating cancer, viral infection, bacterial infection, sepsis, macular degeneration, wounds, depression, a neurodegenerative disorder, trauma, age-related cataracts, organ transplant rejection, an autoimmune disease, or the like, in a patient comprising administering to the patient a therapeutically effective amount of a compound of the invention, or pharmaceutically acceptable salt thereof.

The present invention further provides use of the compounds herein for the production of a medicament for use in therapy.

In another embodiment of the present invention, there is provided a compound having the structure of Formula (II):

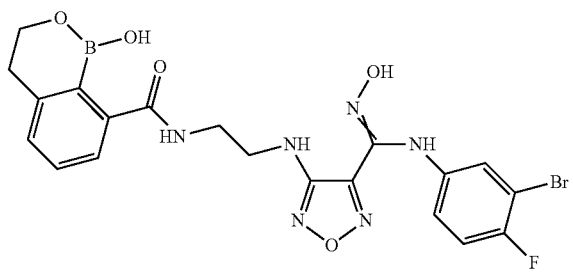

(II)

or pharmaceutically acceptable salt, thereof.

In another embodiment of the present invention, there is provided a compound having the structure of Formula (III):

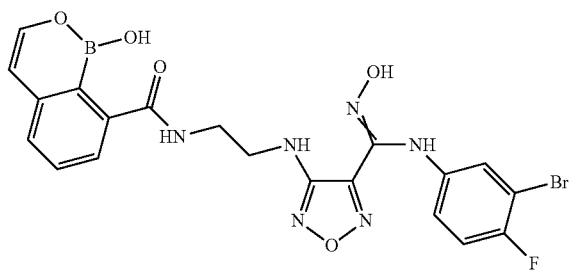

(III)

or pharmaceutically acceptable salt, thereof.

In another embodiment of the present invention, there is provided a compound having the structure of Formula (IV):

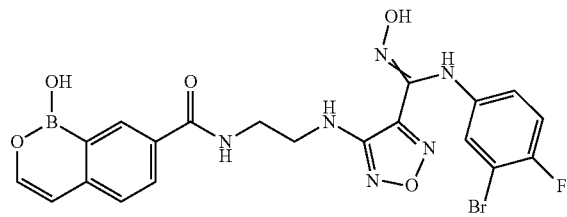

(IV)

or pharmaceutically acceptable salt, thereof.

In another embodiment of the present invention, there is provided a compound having the structure of Formula (V):

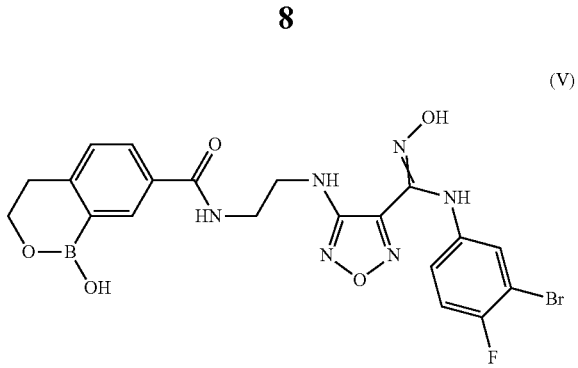

(V)

or pharmaceutically acceptable salt, thereof.

In another embodiment of the present invention, there is provided a compound having the structure of Formula (VI):

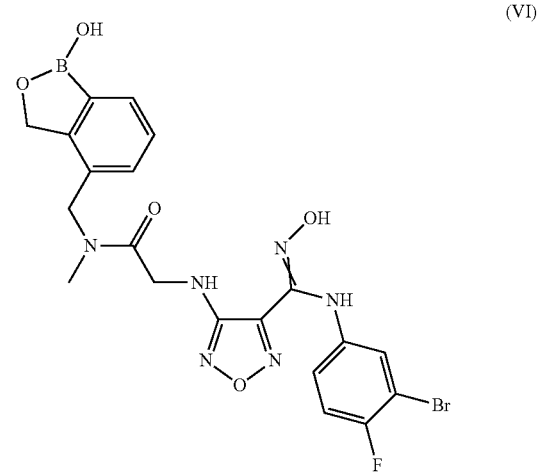 [SMILES: CN(Cc1cccc2c1COB2O)C(=O)CNc1nonc1C(=NO)Nc1ccc(F)c(Br)c1]

(VI)

or pharmaceutically acceptable salt, thereof.

In another embodiment of the present invention, there is provided a compound having the structure of Formula (VII):

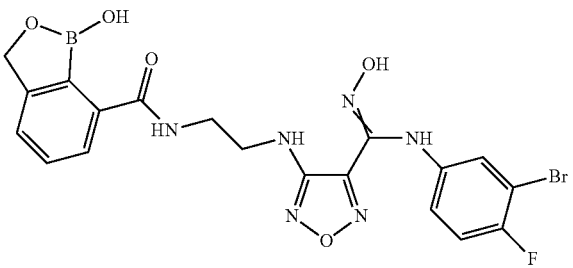

(VII)

or pharmaceutically acceptable salt, thereof.

Such compounds of the present invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formulas I-VII, wherein the compound or salt of the compound is used in the manufacture of a medicament for use in the treatment immunosuppression in a human.

In another embodiment of the invention, there is provided a pharmaceutical composition comprising a pharmaceutically acceptable diluent and a therapeutically effective amount of a compound as defined in Formulas I-VII.

In one embodiment, the pharmaceutical formulation containing a compound of Formulas I-VII or a salt thereof is a formulation adapted for parenteral administration. In another embodiment, the formulation is a long-acting parenteral formulation. In a further embodiment, the formulation is a nano-particle formulation.

The present invention is directed to compounds, compositions and pharmaceutical compositions that have utility as novel treatments for immunosuppresion. While not wanting to be bound by any particular theory, it is thought that the present compounds are able to inhibit the enzyme that catalyzes the oxidative pyrrole ring cleavage reaction of l-Trp to N-formylkynurenine utilizing molecular oxygen or reactive oxygen species.

Therefore, in another embodiment of the present invention, there is provided a method for the prevention and/or treatment of HIV; including the prevention of the progression of AIDS and general immunosuppression.

TABLE 1

| Example No. | Parent Structure | Chemical Name |
|---|---|---|
| 1 | | N-(2-((4-(N-(3-Bromo-4-fluorophenyl)-N'-hydroxycarbamimidoyl)-1,2,5-oxadiazol-3-yl)amino)ethyl)-1-hydroxy-3,4-dihydro-1H-benzo[c][1,2]oxaborinine-8-carboxamide |
| 2 | | N-(2-((4-(N-(3-Bromo-4-fluorophenyl)-N'-hydroxycarbamimidoyl)-1,2,5-oxadiazol-3-yl)amino)ethyl)-1-hydroxy-1H-benzo[c][1,2]oxaborinine-8-carboxamide |
| 3 | | N-(2-((4-(N-(3-Bromo-4-fluorophenyl)-N'-hydroxycarbamimidoyl)-1,2,5-oxadiazol-3-yl)amino)ethyl)-1-hydroxy-1H-benzo[c][1,2]oxaborinine-7-carboxamide |

TABLE 1-continued

| Example No. | Parent Structure | Chemical Name |
|---|---|---|
| 4 | | N-(2-((4-(N-(3-Bromo-4-fluorophenyl)-N'-hydroxycarbamimidoyl)-1,2,5-oxadiazol-3-yl)amino)ethyl)-1-hydroxy-3,4-dihydro-1H-benzo[c][1,2]oxaborinine-7-carboxamide |
| 5 | | 2-((4-(N-(3-Bromo-4-fluorophenyl)-N'-hydroxycarbamimidoyl)-1,2,5-oxadiazol-3-yl)amino)-N-((l-hydroxy-1,3-dihydrobenzo[c][1,2]oxaborol-4-yl)methyl)-N-methylacetamide |
| 6 | | N-(2-((4-(N-(3-Bromo-4-fluorophenyl)-N'-hydroxycarbamimidoyl)-1,2,5-oxadiazol-3-yl)amino)ethyl)-1-hydroxy-1,3-dihydrobenzo[c][1,2]oxaborole-7-carboxamide |

The compounds of the present invention and their salts, solvates, or other pharmaceutically acceptable derivatives thereof, may be employed alone or in combination with other therapeutic agents. The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compound(s) of Formula I-VII or salts thereof and the other pharmaceutically active agent(s) and the relative timings of administration will be selected in order to achieve the desired combined therapeutic effect.

As such, the compounds of the present invention may be used in combination with one or more agents useful in the prevention or treatment of HIV.

Examples of such agents include:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 and BMS-626529, 5-Helix and similar agents;

Integrase inhibitors such as raltegravir, elvitegravir, GSK1349572, GSK1265744 and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

Further examples where_the compounds of the present invention may be used in combination with one or more agents useful in the prevention or treatment of HIV are found in Table 2.

TABLE 2

| FDA Approval | Brand Name | Generic Name | Manufacturer |
|---|---|---|---|
| Nucleosides Reverse Transcriptase Inhibitors (NRTIs) | | | |
| 1987 | Retrovir | zidovudine, azidothymidine, AZT, ZDV | GlaxoSmithKline |
| 1991 | Videx | didanosine, dideoxyinosine, ddI | Bristol-Myers Squibb |
| 1992 | Hivid | zalcitabine, dideoxycytidine, ddC | Roche Pharmaceuticals |
| 1994 | Zerit | stavudine, d4T | Bristol-Myers Squibb |
| 1995 | Epivir | lamivudine, 3TC | GlaxoSmithKline |
| 1997 | Combivir | lamivudine + zidovudine | GlaxoSmithKline |
| 1998 | Ziagen | abacavir sulfate, ABC | GlaxoSmithKline |
| 2000 | Trizivir | abacavir + lamivudine + zidovudine | GlaxoSmithKline |
| 2000 | Videx EC | enteric coated didanosine, ddI EC | Bristol-Myers Squibb |
| 2001 | Viread | tenofovir disoproxil fumarate, TDF | Gilead Sciences |
| 2003 | Emtriva | emtricitabine, FTC | Gilead Sciences |
| 2004 | Epzicom | abacavir + lamivudine | GlaxoSmithKline |
| 2004 | Truvada | emtricitabine + tenofovir disoproxil fumarate | Gilead Sciences |
| Non-Nucleosides Reverse Transcriptase Inhibitors (NNRTIs) | | | |
| 1996 | Viramune | nevirapine, NVP | Boehringer Ingelheim |
| 1997 | Rescriptor | delavirdine, DLV | Pfizer |
| 1998 | Sustiva | efavirenz, EFV | Bristol-Myers Squibb |
| 2008 | Intelence | etravirine | Tibotec Therapeutics |
| Protease Inhibitors (PIs) | | | |
| 1995 | Invirase | saquinavir mesylate, SQV | Roche Pharmaceuticals |
| 1996 | Norvir | ritonavir, RTV | Abbott Laboratories |
| 1996 | Crixivan | indinavir, IDV | Merck |
| 1997 | Viracept | nelfinavir mesylate, NFV | Pfizer |
| 1997 | Fortovase | saquinavir (no longer marketed) | Roche Pharmaceuticals |
| 1999 | Agenerase | amprenavir, APV | GlaxoSmithKline |
| 2000 | Kaletra | lopinavir + ritonavir, LPV/RTV | Abbott Laboratories |
| 2003 | Reyataz | atazanavir sulfate, ATV | Bristol-Myers Squibb |
| 2003 | Lexiva | fosamprenavir calcium FOS-APV | GlaxoSmithKline |
| 2005 | Aptivus | tripranavir, TPV | Boehringer Ingelheim |
| 2006 | Prezista | darunavir | Tibotec Therapeutics |
| Fusion Inhibitors | | | |
| 2003 | Fuzeon | Enfuvirtide, T-20 | Roche Pharmaceuticals & Trimeris |
| Entry Inhibitors | | | |
| 2007 | Selzentry | maraviroc | Pfizer |
| IN Inhibitors | | | |
| 2007 | Isentress | raltegravir | Merck |

The scope of combinations of compounds of this invention with HIV agents is not limited to those mentioned above, but includes in principle any combination with any pharmaceutical composition useful for the treatment of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452.

Ritonavir is 10-hydroxy-2-methyl-5-(1-methyethyl)-1-1 [2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5S*,8R*,10R*,11R*)] and is available from Abbott Laboratories of Abbott park, Illinois, as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism.

GS-9350 is a compound being developed by Gilead Sciences of Foster City Calif. as a pharmacological enhancer.

SPI-452 is a compound being developed by Sequoia Pharmaceuticals of Gaithersburg, Md., as a pharmacological enhancer.

In one embodiment of the present invention, a compound of Formulas I-VII is used in combination with ritonavir. In one embodiment, the combination is an oral fixed dose combination. In another embodiment, the compound of Formulas I-VII is formulated as a long acting parenteral injection and ritonavir is formulated as an oral composition. In one embodiment, is a kit containing the compound of Formulas I-VII formulated as a long acting parenteral injection and ritonavir formulated as an oral composition. In another embodiment, the compound of Formulas I-VII is formulated as a long acting parenteral injection and ritonavir is formulated as an injectable composition. In one embodiment, is a kit containing the compound of Formulas I-VII formulated as a long acting parenteral injection and ritonavir formulated as an injectable composition.

In another embodiment of the present invention, a compound of Formulas I-VII is used in combination with GS-9350. In one embodiment, the combination is an oral fixed dose combination. In another embodiment, the compound of Formulas I-VII is formulated as a long acting parenteral injection and GS-9350 is formulated as an oral composition. In one embodiment, is a kit containing the compound of Formulas I-VII formulated as a long acting parenteral injection and GS-9350 formulated as an oral composition. In another embodiment, the compound of Formulas I-VII is formulated as a long acting parenteral injection and GS-9350 is formulated as an injectable composition. In one embodiment, there is provided a kit containing the compound of Formulas I-VII formulated as a long acting parenteral injection and GS-9350 formulated as an injectable composition.

In one embodiment of the present invention, a compound of Formulas I-VII is used in combination with SPI-452. In one embodiment, the combination is an oral fixed dose combination. In another embodiment, the compound of Formulas I-VII is formulated as a long acting parenteral injection and SPI-452 is formulated as an oral composition. In one embodiment, is a kit containing the compound of Formulas I-VII formulated as a long acting parenteral injection and SPI-452 formulated as an oral composition. In another embodiment, the compound of Formulas I-VII is formulated as a long acting parenteral injection and SPI-452 is formulated as an injectable composition. In one embodiment, is a kit containing the compound of Formulas I-VII formulated as a long acting parenteral injection and SPI-452 formulated as an injectable composition.

EXAMPLES

The following examples serve to more fully describe the manner of making and using the above-described invention. It is understood that these examples in no way serve to limit the true scope of the invention, but rather are presented for illustrative purposes. In the examples and the synthetic schemes below, the following abbreviations have the following meanings. If an abbreviation is not defined, it has its generally accepted meaning.

ACN=acetonitrile
AIBN=azobisisobutyronitrile
aq.=aqueous
µL or uL=microliters
µM or uM=micromolar
NMR=nuclear magnetic resonance
boc=tert-butoxycarbonyl
br=broad
Cbz=Benzyloxycarbonyl
CDI=1,1'-carbonyldiimidazole
d=doublet
δ=chemical shift
° C.=degrees celcius
DCM=dichloromethane
dd=doublet of doublets
DHP=dihydropyran
DIAD=diisopropyl azodicarboxylate
DIEA or DIPEA=N,N-diisopropylethylamine
DMAP=4-(dimethylamino)pyridine
DMEM=Dulbeco's Modified Eagle's Medium
EtOAc=ethyl acetate
h or hr=hours
HATU=1-[Bis(dimethylamino)methylene]-1H-1,2,3-triazolo[4,5-b]pyridinium 3-oxid hexafluorophosphate
HCV=hepatitis C virus
HPLC=high performance liquid chromatography
Hz=hertz
IU=International Units
$IC_{50}$=inhibitory concentration at 50% inhibition
J=coupling constant (given in Hz unless otherwise indicated)
LCMS=liquid chromatography—mass spectrometry
m=multiplet
M=molar
$M+H^+$=parent mass spectrum peak plus $H^+$
MeOH=methanol
mg=milligram
min=minutes
mL=milliliter
mM=millimolar
mmol=millimole
MS=mass spectrum
MTBE=methyl tert-butyl ether
N=normal
NFK=N-formylkynurenine NBS=N-bromosuccinimide
nm=nanomolar
PE=petroleum ether
ppm=parts per million
q.s.=sufficient amount
s=singlet
RT=room temperature
Rf=retardation factor
sat.=saturated
t=triplet
TEA=triethylamine
TFA=trifluoroacetic acid
TFAA=trifluoroacetic anhydride
THF=tetrahydrofuran The compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

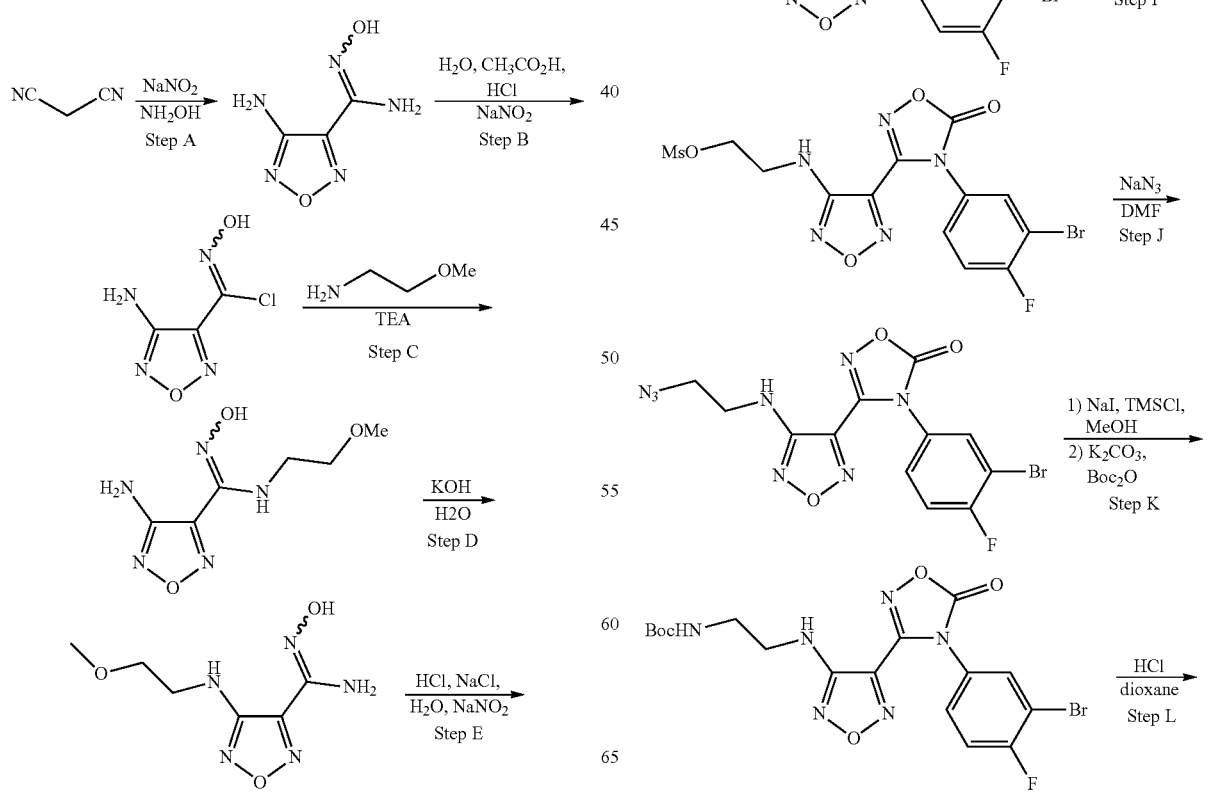

-continued

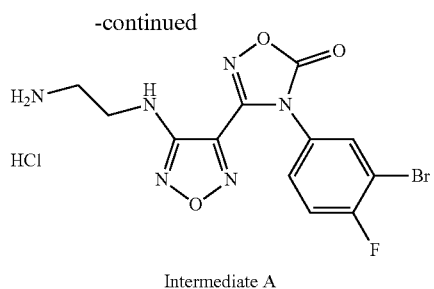

Intermediate A

Intermediate A 3-(4-((2-Aminoethyl)amino)-1,2,5-oxadiazol-3-yl)-4-(3-bromo-4-fluorophenyl)-1,2,4-oxadiazol-5(4H)-one hydrochloride

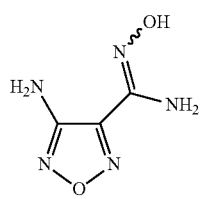

Intermediate A

Step A

4-Amino-N'-hydroxy-1,2,5-oxadiazole-3-carboximidamide

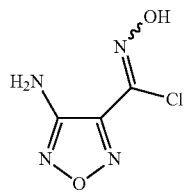

Malononitrile (3.2 kg, 50 mol) was added to water (70 L) preheated to 45° C. and stirred for 5 min. The resulting solution was cooled in an ice bath and sodium nitrite (3.8 kg, 55 mol) was added. When the temperature reached 10° C., 6N hydrochloric acid (550 mL) was added. A mild exothermic reaction ensued with the temperature reaching 16° C. After 15 min the cold bath was removed and the reaction mixture was stirred for 1.5 hrs at 16-18° C. The reaction mixture was cooled to 13° C. and 50% aqueous hydroxylamine (9.9 kg, 150 mol) was added all at once. The temperature rose to 26° C. When the exothermic reaction subsided the cold bath was removed and stirring was continued for 1 hr at 26-27° C., then it was slowly brought to reflux. Reflux was maintained for 2 hrs and then the reaction mixture was allowed to cool overnight. The reaction mixture was stirred in an ice bath and 6N hydrochloric acid (8 L) was added in portions over 40 min to pH 7.0. Stirring was continued in the ice bath at 5° C. The precipitate was collected by filtration, washed well with water and dried in a vacuum oven (50° C.) to give the desired product (5.6 kg, 78%) as an off-white solid. LCMS (M+H)$^+$: m/z=144.1. 1H NMR (400 MHz, DMSO-d6): δ 10.46 (s, 1H), 6.27 (s, 2H), 6.18 (s, 2H).

Step B

4-Amino-N-hydroxy-1,2,5-oxadiazole-3-carbimidoyl chloride

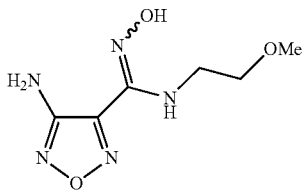 [SMILES: COCCNC(=NO)c1nonc1N]

4-Amino-N'-hydroxy-1,2,5-oxadiazole-3-carboximidamide (4.25 kg, 29.7 mol) was added to a mixture of water (60 L), acetic acid (30 L) and 6N hydrochloric acid (14.75 L) and this suspension was stirred at 42-45° C. until complete solution was achieved. Sodium chloride (5.22 kg, 89.1 mol) was added and this solution was stirred in an ice/water/methanol bath. A solution of sodium nitrite (2.01 kg, 29.1 mol) in water (7 L) was added dropwise over 3.5 hrs while maintaining the temperature below 0° C. After complete addition stirring was continued in the ice bath for 1.5 hrs and then the reaction mixture was allowed to warm to 15° C. The precipitate was collected by filtration, washed well with water, dried in vacuum to give the desired product (2.51 kg, 52%) as an off-white solid. LCMS (M+H)$^+$: m/z=163.1. $^1$H NMR (400 MHz, DMSO-d6): δ 13.38 (s, 1H), 6.29 (s, 2H).

Step C

4-Amino-N'-hydroxy-N-(2-methoxyethyl)-1,2,5-oxadiazole-3-carboximidamide

4-Amino-N-hydroxy-1,2,5-oxadiazole-3-carbimidoyl chloride (2.13 kg, 13.15 mol) was mixed with EtOAc(13 L).

At 0-5° C., 2-methoxyethylamine (1.1 kg, 14.46 mol) was added in one portion while stirring. The reaction temperature rose to 41° C. The reaction was cooled to 0-5° C. TEA (2.0 kg, 19.73 mol) was added. After stirring 5 min, the reaction was washed with water (5 L), brine (5 L), dried over sodium sulfate, and concentrated to give the desired product (1.61 kg, 61%) as a brown oil. LCMS (M+H)+: m/z=202.1. ¹H NMR (400 MHz, DMSO-d6): δ 10.65 (s, 1H), 6.27 (s, 2H), 6.10 (t, J=6.5Hz, 1H), 3.50 (m, 2H), 3.35 (d, J=5. 8Hz, 2H), 3.08 (s, 3H).

Step D

N'-Hydroxy-4-((2-methoxyethyl)ornino)-1,2,5-oxadiazole-3-carboximidamide

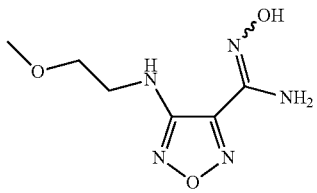

4-Amino-N'-hydroxy-N-(2-methoxyethyl)-1,2,5-oxadiazole-3-carboximidamide (2.56 kg, 12.7 mol) was mixed with water (10 L), potassium hydroxide (2.18 kg, 39 mol) was added. The reaction was refluxed at 100° C. overnight. The reaction was cooled to room temperature and extracted with EtOAc (10L×4), the combined organic solution was dried over sodium sulfate and concentrated to give the desired product (1.87 kg, 73%) as a crude off-white solid. LCMS (M+H)+: m/z=202.1. ¹H NMR (400 MHz, DMSO-d6): δ 10.54 (s, 1H), 6.22(s, 2H), 6.15(t, J=5.8Hz, 1H), 3.45(t, J=5.3Hz, 2H), 3.35 (m, 2H), 3.22 (s, 3H).

Step E

N-Hydroxy-4-((2-methoxyethyl)ornino)-1,2,5-oxadiazole-3-carbimidoyl chloride

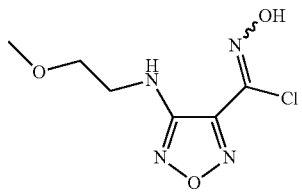

At room temperature, N'-hydroxy-4-((2-methoxyethyl)amino)-1,2,5-oxadiazole-3-carboximidamide (1.87 kg, 9.3 mol) was dissolved in 6N hydrochloric acid aqueous solution (5.12 L). Sodium chloride (1.63 kg, 27.9 mol) was added followed by water (10.2 L) and EtOAc (10.2 L). At 3-5° C. a previously prepared aqueous solution (4.3 L) of sodium nitrite (615 g, 8.8 mol) was added slowly over 1 hr. The reaction was stirred at 3-8° C. for 2 hrs and then room temperature overnight. The reaction mixture was extracted with EtOAc (10L×3). The combined organic solution was dried over sodium sulfate and concentrated to give the desired product (1.5 kg, 73%) as an off-white solid. LCMS (M+H)+: m/z=221.1. ¹H NMR (400 MHz, DMSO-d6): δ 13.43 (s, 1H), 5.85 (t, J=5.6Hz, 1H), 3.50 (t, J=5.6 Hz, 2H), 3.37 (dd, J=10.8, 5.6Hz, 2H), 3.25 (s, 3H).

Step F

N-(3-Bromo-4-fluorophenyl)-N'-hydroxy-4-((2-methoxyethyl)amino)-1,2,5-oxadiazole-3-carboximidamide

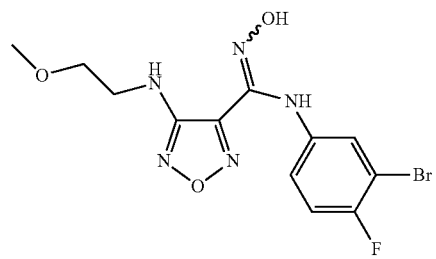 [SMILES: COCCNc1nonc1C(=NO)Nc1ccc(F)c(Br)c1]

N-Hydroxy-4-((2-methoxyethyl)amino)-1,2,5-oxadiazole-3-carbimidoyl chloride (1.5 kg, 6.8 mol) was mixed with water (10 L). The mixture was heated to 60° C. 3-Bromo-4-fluoroaniline (1.44 kg, 7.46 mol) was added and stirred for 10 min. A warm sodium bicarbonate (0.86 kg, 10 mol) solution (10 L water) was added over 15 min. The reaction mixture was stirred at 60° C. for 20 min.

The reaction mixture was cooled to room temperature and extracted with EtOAc (10 L*2). The combined organic solution was dried over sodium sulfate and concentrated to give the desired product (2.3 kg, 90%) as a brown solid. LCMS (M+H)+: m/z=374.0, 376.0. ¹H NMR (400 MHz, DMSO-d6): δ 11.55 (s, 1H), 8.85 (s, 1H), 7.16 (t, J=8. 8Hz, 1H), 7.08 (dd, J=6.1, 2.7Hz, 1H), 6.75 (m, 1H), 6.14 (t, J=5.8Hz, 1H), 3.48 (t, J=5.2Hz, 2H), 3.35 (dd, J=10.8, 5.6Hz, 2H), 3.22 (s, 3H).

Step G 4-(3-Bromo-4-fluorophenyl)-3-(4-((2-methoxyethyl)amino)-1,2,5-oxadiazol-3-yl)-1,2,4-oxadiazol-5(4H)-one

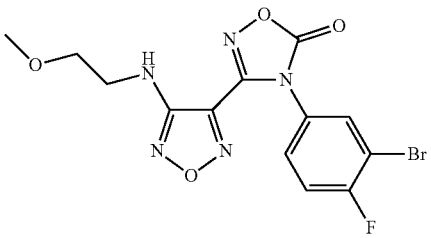 [SMILES: COCCNc1nonc1-c1noc(=O)n1-c1ccc(F)c(Br)c1]

A mixture of N-(3-bromo-4-fluorophenyl)-N'-hydroxy-4-((2-methoxyethyl)amino)-1,2,5-oxadiazole-3-carboximidamide (2.3 kg, 6.15 mol), CDI (1.49 kg, 9.2 mol), and EtOAc (20 L) was heated to 60° C. and stirred for 20 min. The reaction was cooled to room temperature, washed with 1N HCl (2×15 L), dried over sodium sulfate and concentrated to give the desired product (1.95 kg, 80%) as a brown solid. LCMS (M+H)+: m/z=400.0, 402.0. ¹H NMR (400 MHz, DMSO-d6): δ 7.94 (t, J=8.2 Hz, 1H), 7.72 (dd, J=9. 1, 2.3

Hz, 1H), 7.42 (m, 1H), 6.42 (t, J=5.7 Hz, 1H), 3.46 (t, J=5.4Hz, 2H), 3.36 (t, J=5.8Hz, 2H), 3.26 (s, 3H).

Step H 4-(3-Bromo-4-fluorophenyl)-3-(4-((2-hydroxyethyl)amino)-1,2,5-oxadiazol-3-yl)-1,2,4-oxadiazol-5(4H)-one

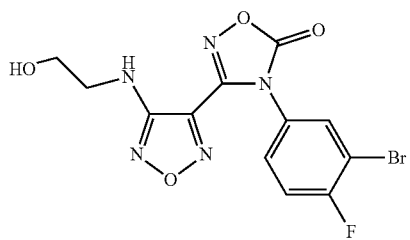

4-(3-Bromo-4-fluorophenyl)-3-(4-((2-methoxyethyl)amino)-1,2,5-oxadiazol-3-yl)-1,2,4-oxadiazol-5(4H)-one (650 g, 1.625 mol) was dissolved in dichloromethane (5L). At −67° C. boron tribromide (313 ml, 3.25 mol) was added over 50 min. The reaction was warmed up to −10° C. in 60 min. The reaction was stirred at room temperature for 1 hour. The reaction was then cooled to −5° C. and slowly quenched with saturated sodium bicarbonate solution (12.5 L) over 2 hours. The reaction temperature rose to 25° C. The reaction was extracted with EtOAc (2×4.5 L). The combined organic layers were dried over sodium sulfate and concentrated to give the desired product (627 g, 100%) as a brown solid. LCMS (M+H)$^+$: m/z=386.0, 388.0. $^1$H NMR (400 MHz, DMSO-d6): δ 8.08 (dd, J=6.2, 2.5 Hz, 1H), 7.70 (m, 1H), 7.68 (t, J=8.7 Hz, 1H), 6.33 (t, J=5.6 Hz, 1H), 4.85 (t, J=5.0 Hz, 1H), 3.56 (dd, J=10.6, 5.6 Hz, 2H), 3.29 (dd, J=11.5, 5.9 Hz, 2H).

Step I 2-((4-(4-(3-Bromo-4-fluorophenyl)-5-oxo-4,5-dihydro-1,2,4-oxadiazol-3-yl)-1,2,5-oxadiazol-3-yl)amino)ethyl methanesulfonate

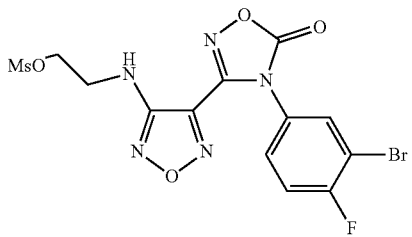

A solution of 4-(3-bromo-4-fluorophenyl)-3-(4-((2-hydroxyethyl)amino)-1,2,5-oxadiazol-3-yl)-1,2,4-oxadiazol-5(4H)-one (1.89 kg, 4.89 mol) in EtOAc (15 L) was treated with the dropwise addition of methanesulfonyl chloride (500 mL, 7.4 mol) over 1 h, at room temperature. Triethylamine (1027 mL, 7.4 mol) was added dropwise over 50 min, during which time the reaction temperature increased to 37° C. After 2 h, the reaction mixture was washed with water (6 L), brine (2 L), dried over sodium sulfate, concentrated to afford the desired product (2.22 kg, 98%) as a brown solid. LCMS (M+Na)$^+$: m/z=485.9, 487.9. $^1$H NMR (400 MHz, DMSO-d6): δ 8.08 (dd, J=6.2, 2.5 Hz, 1H), 7.72 (m, 1H), 7.58 (t, J=8.7 Hz, 1H), 6.75 (t, J=5.7 Hz, 1H), 4.36 (t, J=5.3 Hz, 2H), 3.58 (dd, J=11.2, 5.6 Hz, 2H), 3.18 (s, 3H).

Step J 3-(4-((2-Azidoethyl)amino)-1,2,5-oxadiazol-3-yl)-4-(3-bromo-4-fluorophenyl)-1,2,4-oxadiazol-5(4H)-one

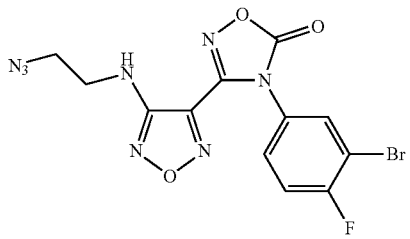 [SMILES: O=c1onc(-c2nonc2NCCO)n1-c1ccc(F)c(Br)c1]

A solution of 2-((4-(4-(3-bromo-4-fluorophenyl)-5-oxo-4,5-dihydro-1,2,4-oxadiazol-3-yl)-1,2,5-oxadiazol-3-yl)amino)ethyl methanesulfonate (2.22 kg, 4.8 mol) in dimethylformamide (4 L) stirring in a 22 L flask was treated with sodium azide (400 g, 6.15 mol). The reaction was heated at 50° C. overnight. The reaction mixture was poured into ice/water (8 L), and extracted with 1:1 ethyl acetate:heptane (20 L). The organic layer was washed with water (5 L), and brine (5 L), and the solvents removed in vacuo to afford the desired product (1.7 kg, 86%) as a tan solid. LCMS (M+Na)$^+$: m/z=433.0, 435.0. $^1$H NMR (400 MHz, DMSO-d6): δ 8.08 (dd, J=6.2, 2.5Hz, 1H), 7.72 (m, 1H), 7.58 (t, J=8.7 Hz, 1H), 6.75 (t, J=5.7 Hz, 1H), 3.54 (t, J=5.3 Hz, 2H), 3.45 (dd, J=11.1, 5.2 Hz, 2H).

Step K tert-Butyl (2-((4-(4-(3-bromo-4-fluorophenyl)-5-oxo-4,5-dihydro-1,2,4-oxadiazol-3-yl)-1,2,5-oxadiazol-3-yl)amino)ethyl)carbamate

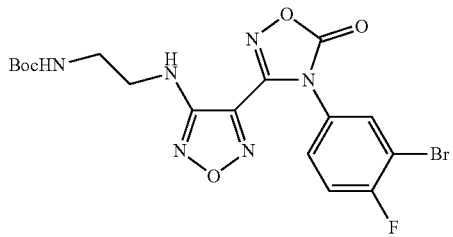 [SMILES: CC(C)(C)OC(=O)NCCNc1nonc1-c1noc(=O)n1-c1ccc(F)c(Br)c1]

Sodium iodide (4.09 kg, 27.3 mol) was added to 3-(4-((2-azidoethyl)amino)-1,2,5-oxadiazol-3-yl)-4-(3-bromo-4-fluorophenyl)-1,2,4-oxadiazol-5(4H)-one (1.7 kg, 4.1 mol) in methanol (23 L). The mixture was stirred for 30 min during which time a mild exotherm was observed. Chlorotrimethylsilane (3.53 L, 27.8 mol) was added as a solution in methanol (3.5 L) dropwise at a rate so that the temperature did not exceed 35° C., and the reaction was stirred for 3.5 h at ambient temperature. The reaction was neutralized with 33 wt % solution of sodium thiosulfate pentahydrate in water (5.7 L), diluted with water (15 L), and the pH adjusted to 9 carefully with solid potassium carbonate (1.15 kg, 8.33 mol). Di-tert-butyl dicarbonate (1.205 kg, 5.52 mol) was added and the reaction was allowed to stir at room temperature. Additional potassium carbonate (750 g, 5.41 mol) was added in 150g portions over 4 h to ensure that the pH was maintained at or above 9. After stirring at room temperature overnight, the solid was filtered, triturated with water (7.8 L), and then MTBE (6 L). Then the solid was triturated with 1:1 THF:dichloromethane (6 L, in a 22 L rotary evaporator flask, 50° C., 1 h), filtered and washed with dichloromethane (3 L) to afford an off-white solid. The crude material was dissolved at 55° C. tetrahydrofuran (5 mL/g), treated with decolorizing carbon (2 wt %) and silica gel (2 wt %), and filtered hot through celite to afford the product (1720 g, 86%) as a off-white solid. LCMS (M+Na)$^+$: m/z=506.8, 508.8. $^1$H NMR (400 MHz, DMSO-d6): δ 8.08 (dd, J=6.2, 2.5Hz, 1H), 7.72 (m, 1H), 7.60 (t, J=8.7 Hz, 1H), 6.94 m, 1H), 6.52 (m, 1H), 3.30 (m, 2H), 3.18 (m, 2H), 1.38 (s, 9H).

Step L 3-(4-((2-Aminoethyl)amino)-1,2,5-oxadiazol-3-yl)-4-(3-bromo-4-fluorophenyl)-1,2,4-oxadiazol-5(4H)-one hydrochloride Intermediate A

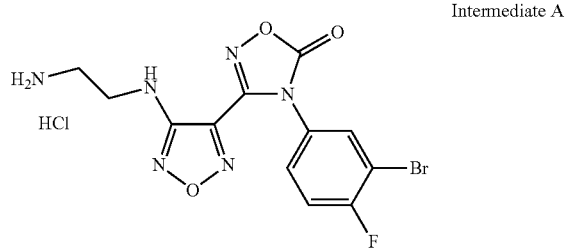 [SMILES: NCCNc1nonc1-c1noc(=O)n1-c1ccc(F)c(Br)c1 ; Cl]

A 22 L flask was charged hydrogen chloride (3 N solution in 1,4-dioxane, 4 L, 12 mol). tert-butyl (2-((4-(4-(3-bromo-4-fluorophenyl)-5-oxo-4,5-dihydro-1,2,4-oxadiazol-3-yl)-1,2,5-oxadiazol-3-yl)amino)ethyl)carbamate (1.72 kg, 3.54 mol) was added was a solid in portions over 10 min. The slurry was stirred at room temperature and gradually became a thick paste that could not be stirred. After sitting overnight at room temperature, the paste was slurried in EtOAc (10 L), filtered, and dried to afford the desired product (1.38 kg, 93%) as a white solid. $^1$H NMR (400 MHz, DMSO-d6): δ 8.12 (m, 4H), 7.76 (m, 1H), 7.58 (t, J=8.7 Hz, 1H), 6.78 (t, J=6.1 Hz, 1H), 3.51 (dd, J=11.8, 6.1 Hz, 2H), 3.02 (m, 2H). LCMS (M+H)$^+$: m/z=384.9, 386.9.

Scheme II: Synthesis of Intermediate B

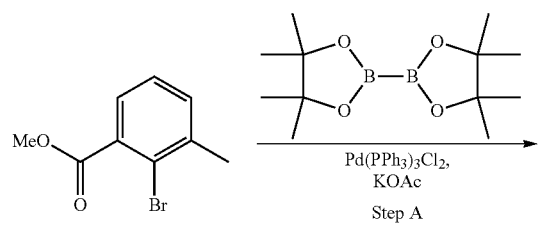

Pd(PPh$_3$)$_3$Cl$_2$, KOAc

Step A

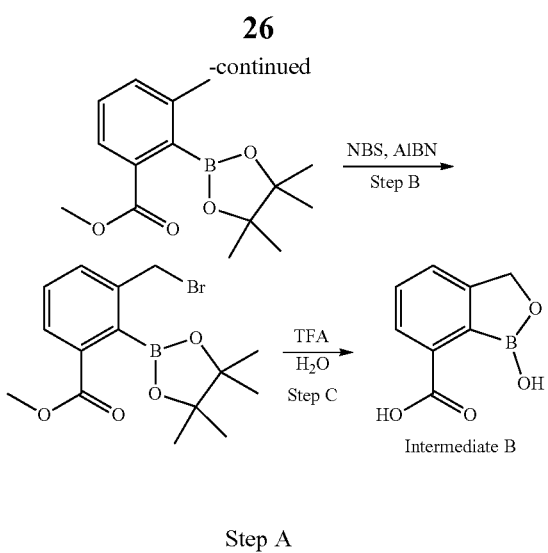

Step A

Methyl 3-methyl-2-(4,4,5,5-tetramethyl-1,3,2-dioxaborolon-2-yl)benzoote

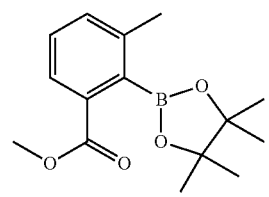

A solution of methyl 2-bromo-3-methylbenzoate (5 g, 21.83 mmol) in dioxane (100 mL) was treated with bis(pinacolato)diboron (6.65 g, 26.2 mmol) and potassium acetate (6.43 g, 65.5 mmol). The mixture was degassed with N$_2$ and added bis(triphenylphosphine)palladium(II) chloride (1.532 g, 2.183 mmol) heated at 90° C. for 22 h. After the reaction was cooled to room temperature it was filtered through a short pad of celite. The filtrate was concentrated, and the residue was purified by silica gel chromatography (10% EtOAc/hexane) to give methyl 3-methyl-2-(4,4,5,5-tetramethyl-1,3,2-dioxaborolan-2-yl)benzoate (4.3 g, 14.01 mmol, 64.2% yield) as a solid. $^1$H NMR (400 MHz, CHLOROFORM-d) δ ppm 1.44 (s, 12 H) 2.43 (s, 3 H) 3.89 (s, 3 H) 7.22-7.33 (m, 2 H) 7.76 (d, J=7.43 Hz, 1 H). LCMS (M+H)$^+$: m/z=277.3.

Step B

Methyl 3-(bromomethyl)-2-(4,4,5,5-tetramethyl-1,3,2-dioxaborolon-2-yl)benzoate

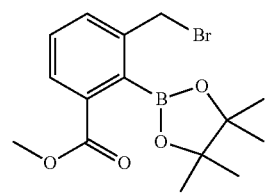

A solution of methyl 3-methyl-2-(4,4,5,5-tetramethyl-1,3,2-dioxaborolan-2-yl)benzoate (4.8 g, 13.91 mmol) in carbon tetrachloride (100.0 mL) was treated with NBS (4.27 g, 24.01 mmol) followed by AIBN (0.717 g, 4.37 mmol). The mixture was heated at reflux for 6 h. The solvent was removed and the crude material was purified by silica gel chromatography (20% EtOAc/Hexanes) to afford methyl 3-(bromomethyl)-2-(4,4,5,5-tetramethyl-1,3,2-dioxaborolan-2-yl)benzoate (5.15 g, 10.15 mmol, 46.5% yield, 70% purity) as a solid. $^1$H NMR (400 MHz, CHLOROFORM-d) δ ppm 1.47 (s, 12 H) 3.90 (s, 3 H) 4.58 (s, 2 H) 7.38 (t, J=7.72 Hz, 1 H) 7.53-7.58 (m, 1 H) 7.87 (d, J=7.62 Hz, 1 H).

Step C

1-Hydroxy-1,3-dihydrobenzo[c][1,2]oxaborole-7-carboxylic acid

Intermediate B

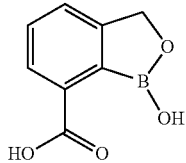

A solution of methyl 3-(bromomethyl)-2-(4,4,5,5-tetramethyl-1,3,2-dioxaborolan-2-yl)benzoate (3.9 g, 10.98 mmol) in the mixture of ACN (10.0 mL) and water (10.0 mL) was treated with trifluoroacetic acid (10.09 mL, 131 mmol) and stirred at 70° C. for 16 h. After removal of acetonitrile the mixture, the reaction was neutralized to pH 7 with aq. NaHCO$_3$ and extracted with EtOAc (3×50 mL). The combined organics were discarded. The aqueous layer was then acidified with 1N HCl and extract with EtOAc (4×50 mL). The combined organic layers were washed with water, brine, dried over Na$_2$SO$_4$ and evaporated the solvent afforded 1-hydroxy-1,3-dihydrobenzo[c][1,2]oxaborole-7-carboxylic acid (1.4 g, 7.08 mmol, 32.4% yield) as a solid. $^1$H NMR (400 MHz, DMSO-d$_6$) δ ppm 5.09 (s, 2 H) 7.58-7.68 (m, 1 H) 7.69-7.75 (m, 1 H) 7.98 (d, J=7.43 Hz, 1 H) 8.86 (br. s., 1 H). LCMS (M+H)$^+$: m/z=179.1.

Scheme III: Synthesis of Intermediate C

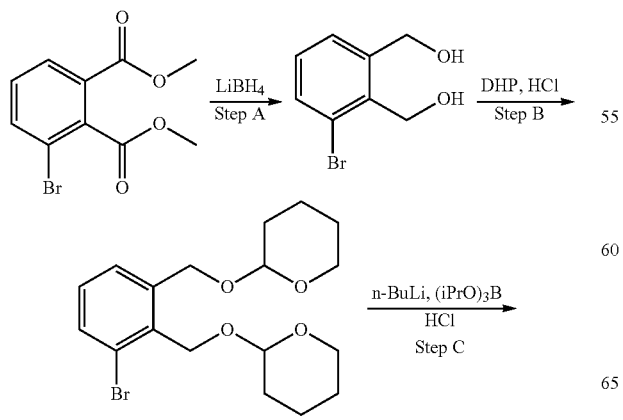

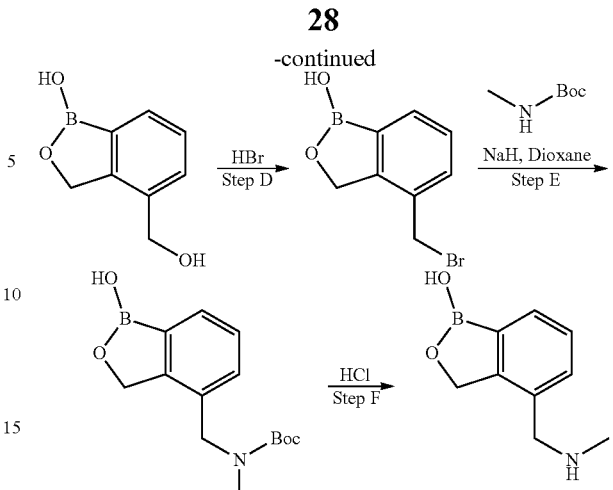

Step A (3-Bromo-1,2-phenylene)dimethanol

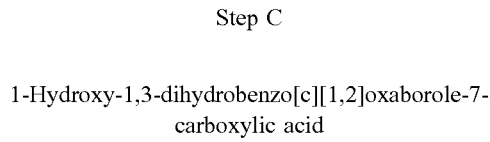

A solution of dimethyl 3-bromophthalate, CAS# 58749-33-0 or made according to preparation in US2007049618, (20 g, 73.5 mmol) in ether (60 mL) was cooled to 0° C. and treated by the dropwise addition of LiBH$_4$ (6.3 g, 220.6 mmol) in THF (140 mL) for a period of 1 hr. The reaction mixture stirred for overnight at room temperature. The reaction was poured into ice water and acidified with concentrated HCl to pH=2. The organic layer was extracted with EtOAc (3×200 mL), dried over Na$_2$SO$_4$, and concentrated to give (3-bromo-1,2-phenylene)dimethanol (4.7 g, 30%) as a white solid. Rf=0.1 (30% EtOAc/PE).

Step B 2,2'-(((3-Bromo-1,2-phenylene)bis(methylene))bis(oxy))bis(tetrahydro-2H-pyran)

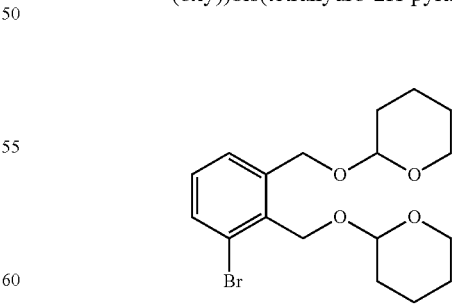

A solution of (3-bromo-1,2-phenylene)dimethanol (15 g, 69.1 mmol) in DHP (75 mL) was treated with concentrated HCl (0.3 mL). The reaction was stirred at room temperature for 12 hours. The reaction was then diluted with EtOAc (300 mL) and washed with water (800 mL). The organic layer was dried over Na$_2$SO$_4$ and concentrated under reduced pressure. The residue was purified by silica gel chromatography (2% EtOAc/PE) to give 2,2'-(((3-bromo-1,2-phenylene)bis(methylene))bis(oxy))bis(tetrahydro-2H-pyran) (28 g, 100%) as a light yellow liquid. Rf=0.4 (30% EtOAc/PE).

Step C 4-(Hydroxymethyl)benzo[c][1, 2]oxaborol-1(3H)-ol

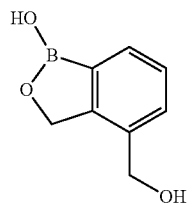 [SMILES: OCc1cccc2c1COB2O]

A solution of 2,2'-(((3-bromo-1,2-phenylene)bis(methylene))bis(oxy))bis(tetrahydro-2H-pyran) (14 g, 36.5 mmol) in THF (186 mL) was cooled to −78° C., then treated by the dropwise addition of n-BuLi (16.4 mL, 40.1 mmol). The mixture was stirred for 30 min. then treated with the dropwise addition of (iPrO)$_3$B (53.6 mL, 219.6 mmol) at the same temperature. The reaction was then allowed to stir with warming to room temperature overnight. The reaction was treated with concentrated HCl (84 mL) and stirred overnight. The reaction was then diluted with water (200 mL) and extracted with EtOAc (2×200 mL) and then basified with saturated Na$_2$SO$_3$ and separated the organic layer and acidified with dilute HCl (pH=2) and extracted with EtOAc (2×200 mL). The separated organic layer was dried over Na$_2$SO$_4$ and concentrated under reduced pressure to give 4-(hydroxymethyl)benzo[c][1,2]oxaborol-1(3H)-ol (2.13 g, 36%) as an off white solid. Rf=0.1 (5% MeOH/CHCl$_3$).

Step D 4-(Bromomethyl)benzo[c][1,2]oxaborol-1(3H)-ol

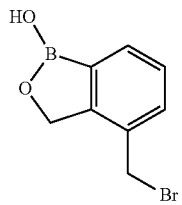

A flask containing 4-(hydroxymethyl)benzo[c][1,2]oxaborol-1(3H)-ol (1.0 g, 6.1 mmol) was treated with aqueous HBr (10 mL, 10M). The reaction was stirred at room temperature overnight. The reaction was diluted with water and the solids filtered rinsing with water and dried to give 4-(bromomethyl)benzo[c][1,2]oxaborol-1(3H)-ol (1.2 g, 87%) as a white solid. Rf=0.6 (5% MeOH/CHCl$_3$).

Step E tert-Butyl ((1-hydroxy-1,3-dihydrobenzo[c][1,2]oxaborol-4-yl)methyl)(methyl)carbomate

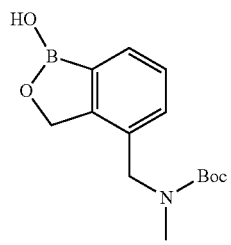 [SMILES: CN(Cc1cccc2c1COB2O)C(=O)OC(C)(C)C]

A flask containing NaH (0.42 g, 17.5 mmol) washed with n-hexanes, was treated with tert-butyl methylcarbamate (1.15 g, 8.7 mmol) in dioxanes (15 mL) and stirred for 30 min. The flask was then treated by the addition of 4-(bromomethyl)benzo[c][1,2]oxaborol-1(3H)-ol (1 g, 4.3 mmol) at 10° C., then the reaction was stirred at room temperature for 8 hours. The reaction was then quenched with the addition of ice cold water and extracted with ether. The organics were set aside, and the aqueous was acidified with 1N HCl and extracted with EtOAc, dried over Na$_2$SO$_4$ and concentrated under reduced pressure to give tert-butyl ((1-hydroxy-1,3-dihydrobenzo[c][1,2]oxaborol-4-yl)methyl)(methyl)carbamate (1 g, 82%) as a thick liquid.

Step F 4-((Methylamino)methyl)benzo[c][1,2]oxaborol-1(3H)-ol

Intermediate C

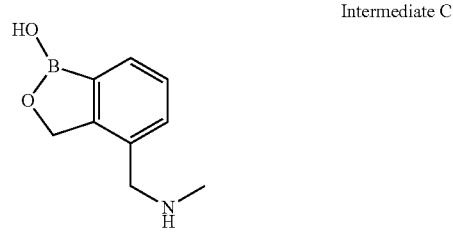

A flask containing tert-butyl ((1-hydroxy-1,3-dihydrobenzo[c][1,2]oxaborol-4-yl)methyl)(methyl)carbamate (1 g, 3.6 mmol) was treated with concentrated HCl (10 mL) and stirred for 4 hours. The solvents were distilled out and dried under reduced pressure to give a residue. The reside was recrystallized in acetone to give 4-((methylamino)methyl)benzo[c][1,2]oxaborol-1(3H)-ol (0.3 g, 48%) as a brown solid.

Scheme IV: Synthesis of Compound 1

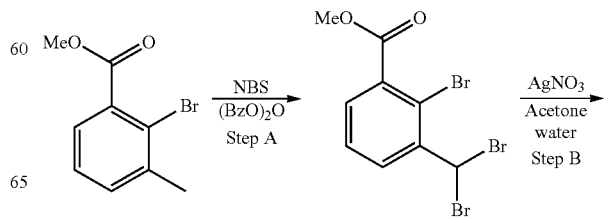

-continued

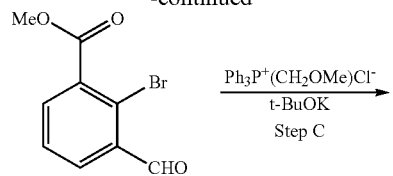
Ph₃P⁺(CH₂OMe)Cl⁻
t-BuOK
Step C

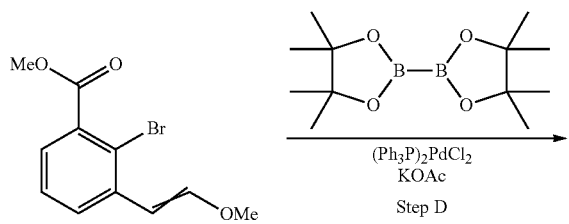
(Ph₃P)₂PdCl₂
KOAc
Step D

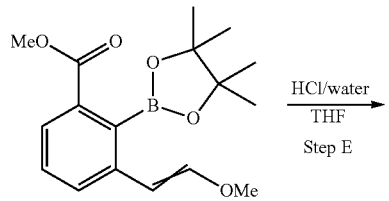
HCl/water
THF
Step E

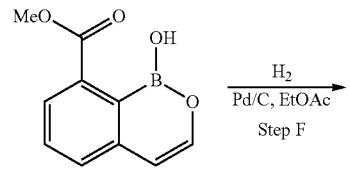
H₂
Pd/C, EtOAc
Step F

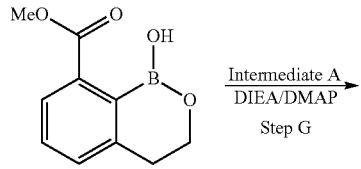
Intermediate A
DIEA/DMAP
Step G

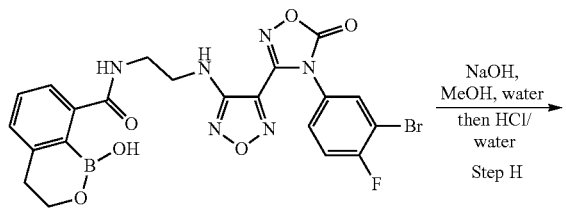
NaOH,
MeOH, water
then HCl/
water
Step H

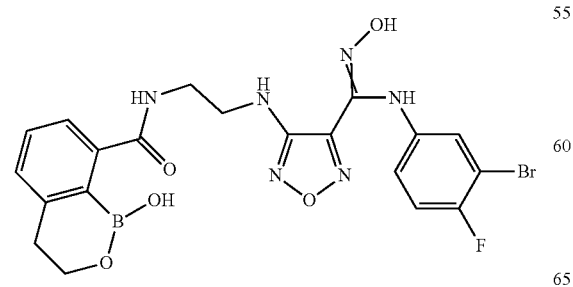

1

Example 1

Compound 1

N-(2-((4-(N-(3-bromo-4-fluorophenyl)-N'-hydroxy-carbamimidoyl)-1,2,5-oxadiazol-3-yl)amino)ethyl)-1-hydroxy-3,4-dihydro-1H-benzo[c][1,2]oxaborinine-8-carboxamide

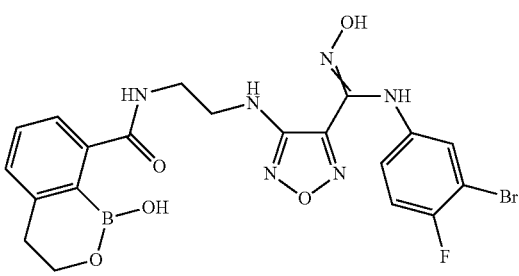

1

Step A

Methyl 2-bromo-3-(dibromomethyl)benzoate

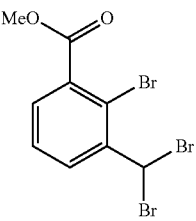 [SMILES: COC(=O)c1cccc(C(Br)Br)c1Br]

To a solution of methyl 2-bromo-3-methylbenzoate (8.0 g, 34.2 mmol) in carbon tetrachloride (100 mL) was added NBS (18.27 g, 103 mmol) followed by benzoyl peroxide (1.658 g, 6.85 mmol) and the mixture was stirred at 75° C. under nitrogen atmosphere for 3.5 h. The mixture was concentrated, triturated with diethyl ether and filtered. The filtrate was dissolved in 1:1 diethyl ether/hexanes and washed with water. The organic phase was dried (Na₂SO₄), concentrated, dried in vacuo to provide methyl 2-bromo-3-(dibromomethyl)benzoate (14.0 g, 34.8 mmol, 98% yield) as a yellowish solid. ¹1-1 NMR (400 MHz, CHLOROFORM-d) δ ppm 2.79 (s, 1 H) 3.97 (s, 3 H) 7.46-7.52 (m, 1 H) 7.64 (dd, J=7.65, 1.63 Hz, 1 H) 8.20 (dd, J=8.03, 1.51 Hz, 1 H). LC/MS (m/z) ES⁺: 386.9, 389.0 (M+1)⁺.

Step B

Methyl 2-bromo-3-formylbenzoate

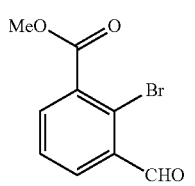

To a solution of methyl 2-bromo-3-(dibromomethyl)benzoate (17.62 g, 45.5 mmol) in acetone (200 mL) was added silver nitrate (23.21 g, 137 mmol) and water (50 mL). The suspension was stirred at ambient temperature in the dark for 1 h. The silver salts were removed by filtration and the filtrate diluted with EtOAc, washed with brine, saturated sodium bicarbonate and water. The organic layer was dried (Na$_2$SO$_4$), concentrated and purified on silica (EtOAc/hexanes, 0-20%) to obtain methyl 2-bromo-3-formylbenzoate (9.0 g, 37.0 mmol, 81% yield) as a white solid. $^1$1-1 NMR (400 MHz, CHLOROFORM-d) δ ppm 4.01 (s, 3 H) 7.52 (t, J=7.65 Hz, 1 H) 7.92 (dd, J=7.53, 1.76 Hz, 1 H) 8.04 (dd, J=7.53, 1.76 Hz, 1 H) 10.53 (s, 1 H). LC/MS (m/z) ES$^+$ : 243.0, 245.1 (M+1)$^+$.

Step C

Methyl 2-bromo-3-(2-methoxyvinyl)benzoate

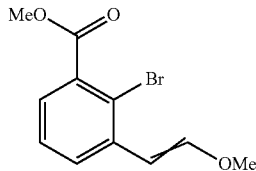 [SMILES: COC=Cc1cccc(C(=O)OC)c1Br]

To a suspension of potassium t-butoxide (5.73 g, 51.1 mmol) in THF (130 mL) under nitrogen atmosphere was added (methoxymethyl)triphenylphosphonium chloride (17.52 g, 51.1 mmol) and the deep-red mixture was stirred at ambient temperature for 45 min and then methyl 2-bromo-3-formylbenzoate (6.21 g, 25.5 mmol) was added in one portion. Stirring at ambient temperature continued for 2 h. Saturated NH$_4$Cl/water and EtOAc were added and the organic phase was dried (Na$_2$SO$_4$), concentrated, and purified on silica gel (EtOAc/hexanes, 0-5%) to provide methyl 2-bromo-3-(2-methoxyvinyl)benzoate (6.53 g, 24.09 mmol, 94% yield) as an E/Z mixture. $^1$H NMR (400 MHz, CHLOROFORM-d) δ ppm 3.77 (s, 3 H) 3.82 (s, 3 H) 3.96 (d, J=3.51 Hz, 6 H) 5.72 (d, J=7.28 Hz, 1 H) 6.20 (d, J=12.80 Hz, 1 H) 6.32 (d, J=7.28 Hz, 1 H) 6.98 (d, J=12.80 Hz, 1 H) 7.25-7.34 (m, 2 H) 7.39-7.48 (m, 3 H) 8.14 (dd, J=7.91, 1.63 Hz, 1 H). LC/MS (m/z) ES$^+$ : 271.1, 273.1 (M+1)$^+$.

Step D

Methyl 3-(2-methoxyyinyl)-2-(4,4,5,5-tetramethyl-1,3,2-dioxaborolan-2-yl)benzoate

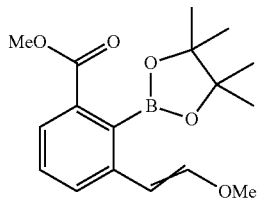 [SMILES: COC=Cc1cccc(C(=O)OC)c1B1OC(C)(C)C(C)(C)O1]

A mixture of methyl 2-bromo-3-(2-methoxyvinyl)benzoate (6.5 g, 22.30 mmol), bis(pinacolato)diboron (6.23 g, 24.53 mmol), potassium acetate (6.56 g, 66.9 mmol), 1,4-dioxane (170 mL) and bis(triphenylphosphine)palladium(II) chloride (4.70 g, 6.69 mmol) was degassed with a stream of nitrogen for 10 min, placed in a sealed tube and heated at 95° C. for 28 h. The mixture was filtered and the filtrate was partitioned between EtOAc and water. The organic phase was dried (Na$_2$SO$_4$), concentrated and purified on silica gel using (EtOAc/hexanes, 0-10%) to provide methyl 3-(2-methoxyvinyl)-2-(4,4,5,5-tetramethyl-1,3,2-dioxaborolan-2-yl)benzoate (4.39 g, 13.80 mmol, 62% yield) as an E/Z mixture. $^1$H NMR (400 MHz, CHLOROFORM-d) δ ppm 1.48 (d, J=3.76 Hz, 24 H) 3.72 (s, 3 H) 3.79 (s, 3 H) 3.93 (d, J=2.76 Hz, 6 H) 5.46 (d, J=7.28 Hz, 1 H) 6.06 (d, J=12.80 Hz, 1 H) 6.21 (d, J=7.28 Hz, 1 H) 6.98 (d, J=12.80 Hz, 1 H) 7.30-7.40 (m, 2 H) 7.48 (d, J=7.78 Hz, 1 H) 7.73-7.83 (m, 2 H) 8.19 (d, J=7.78 Hz, 1 H). LC/MS (m/z) ES$^+$ : 341.3 (M+23)$^+$.

Step E

Methyl 1-hydroxy-1H-benzo[c][1,2]oxaborinine-8-carboxylate

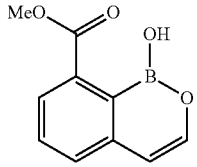

To a solution of methyl 3-(2-methoxyvinyl)-2-(4,4,5,5-tetramethyl-1,3,2-dioxaborolan-2-yl)benzoate (4.14 g, 12.75 mmol) in tetrahydrofuran (90 mL) was added 4N HCl/water (31.9 mL, 128 mmol) and the mixture was stirred at 60° C. for 3 h. The mixture was partitioned between EtOAc and water. The organic phase was washed with water (4×), dried (Na$_2$SO$_4$), concentrated to provide methyl 1-hydroxy-1H-benzo[c][1,2]oxaborinine-8-carboxylate (2.12 g, 9.56 mmol, 75.0% yield) as a pale yellow semi-solid. $^1$H NMR (400 MHz, CHLOROFORM-d) δ ppm 4.01 (s, 3 H) 6.26 (d, J=5.27 Hz, 1 H) 7.14 (d, J=5.24 Hz, 1 H) 7.53-7.68 (m, 2 H) 8.18 (dd, J=7.26, 1.30 Hz, 1 H) 10.27 (s, 1 H). LC/MS (m/z) ES$^+$ : 205.1 (M+1)$^+$.

Step F

Methyl 1-hydroxy-3,4-dihydro-1H-benzo[c][1,2]oxaborinine-8-carboxylate

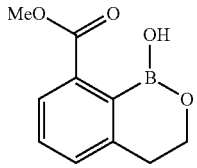

To a solution of methyl 1-hydroxy-1H-benzo[c][1,2]oxaborinine-8-carboxylate (2.1 g, 9.47 mmol) in EtOAc (80 mL) was added 10% Pd-C (1.008 g, 0.947 mmol) and the mixture was stirred under hydrogen atmosphere at ambient temperature for 1 h. The mixture was filtered washing with EtOAc and MeOH. The filtrate was concentrated, dried in vacuo to provide methyl 1-hydroxy-3,4-dihydro-1H-benzo[c][1,2]oxaborinine-8-carboxylate (1.99 g, 8.98 mmol, 95% yield) as a clear oil. ¹H NMR (400 MHz, CHLOROFORM-d) δ ppm 2.99 (s, 2 H) 3.96 (s, 3 H) 4.09-4.17 (m, 2 H) 7.36-7.62 (m, 2 H) 7.95 (d, J=7.53 Hz, 1 H) 9.04-9.47 (m, 1 H). LC/MS (m/z) ES⁺ : 207.2 (M+1)⁺.

Step G

N-(2-((4-(4-(3-Bromo-4-fluorophenyl)-5-oxo-4,5-dihydro-1,2,4-oxadiazol-3-yl)-1,2,5-oxadiazol-3-yl)amino)ethyl)-1-hydroxy-3,4-dihydro-1H-benzo[c][1,2]oxaborinine-8-carboxamide

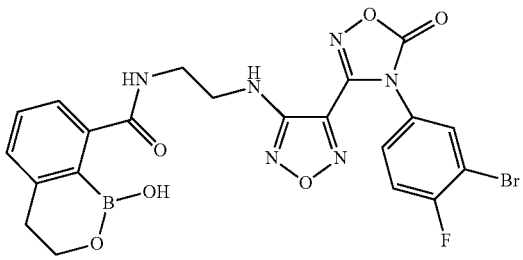 [SMILES: O=C(NCCNc1nonc1-c1noc(=O)n1-c1ccc(F)c(Br)c1)c1cccc2c1B(O)OCC2]

A mixture of methyl 1-hydroxy-3,4-dihydro-1H-benzo[c][1,2]oxaborinine-8-carboxylate (220 mg, 0.929 mmol), 3-(4-((2-aminoethyl)amino)-1,2,5-oxadiazol-3-yl)-4-(3-bromo-4-fluorophenyl)-1,2,4-oxadiazol-5(4H)-one, Hydrochloride, intermediate A (392 mg, 0.929 mmol), MeOH (8 mL), DIEA (0.974 mL, 5.57 mmol) and DMAP (45.4 mg, 0.372 mmol) was stirred under nitrogen atmosphere at 80° C. for 18 h. The mixture was concentrated, dissolved in EtOAc and washed with 1N HCl/water. The organic phase was dried (Na₂SO₄), concentrated and purified by reverse phase C18 HPLC (10-60% ACN/water, 0.2% formic acid) to provide N-(2-((4-(4-(3-bromo-4-fluorophenyl)-5-oxo-4,5-dihydro-1,2,4-oxadiazol-3-yl)-1,2,5-oxadiazol-3-yl)amino)ethyl)-1-hydroxy-3,4-dihydro-1H-benzo[c][1,2]oxaborinine-8-carboxamide (336 mg, 0.589 mmol, 63.4% yield) as an off-white solid. ¹H NMR (400 MHz, DMSO-c/₆) δ ppm 2.92 (t, J=5.65 Hz, 2 H) 3.42-3.60 (m, 4 H) 3.99 (t, J=5.77 Hz, 2 H) 6.60 (t, J=5.77 Hz, 1 H) 7.34-7.45 (m, 2 H) 7.46-7.53 (m, 1 H) 7.58-7.68 (m, 1 H) 7.74-7.84 (m, 1 H) 8.14 (dd, J=6.15, 2.38 Hz, 1 H) 8.68 (t, J=5.52 Hz, 1 H) 9.18 (s, 1 H). LC/MS (m/z) ES⁺ : 559.2, 561.3 (M+1)⁺.

Step H

N-(2-((4-(N-(3-Bromo-4-fluorophenyl)-N'-hydroxycarbamimidoyl)-1,2,5-oxadiazol-3-yl)amino)ethyl)-1-hydroxy-3,4-dihydro-1H-benzo[c][1,2]oxaborinine-8-carboxamide

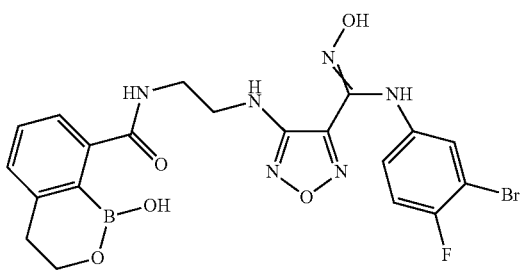

1

N-(2-((4-(4-(3-Bromo-4-fluorophenyl)-5-oxo-4,5-dihydro-1,2,4-oxadiazol-3-yl)-1,2,5-oxadiazol-3-yl)amino)ethyl)-1-hydroxy-3,4-dihydro-1H-benzo[c][1,2]oxaborinine-8-carboxamide (260 mg, 0.451 mmol) in methanol (3 mL) was added 2M NaOH/water (0.541 mL, 1.353 mmol) and the mixture was stirred at ambient temperature for 20 min then concentrated. A small amount of water was added and the clear solution was treated with 3N HCl/water to pH~2. The solid was filtered, washed with water and dried in vacuo to provide N-(2-((4-(N-(3-bromo-4-fluorophenyl)-N'-hydroxycarbamimidoyl)-1,2,5-oxadiazol-3-yl)amino)ethyl)-1-hydroxy-3,4-dihydro-1H-benzo[c][1,2]oxaborinine-8-carboxamide (220 mg, 0.409 mmol, 91% yield) as an off-white solid. ¹H NMR (400 MHz, DMSO-d₆) δ ppm 2.91 (t, J=5.52 Hz, 2 H) 3.43-3.58 (m, 4 H) 4.01 (t, J=5.65 Hz, 2 H) 6.35 (t, J=5.65 Hz, 1 H) 6.72-6.81 (m, 1 H) 7.10-7.20 (m, 2 H) 7.33-7.52 (m, 3 H) 8.68-8.76 (m, 1 H) 8.94 (s, 1 H) 9.12 (br. s., 1 H) 11.40 (s, 1 H). LC/MS (m/z) ES⁺ : 533 (M+1)⁺.

Scheme V: Synthesis of Compound 2

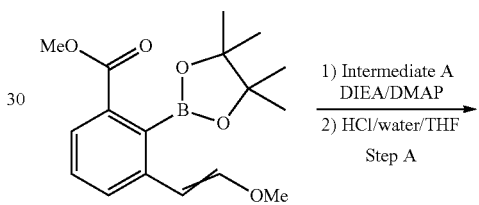

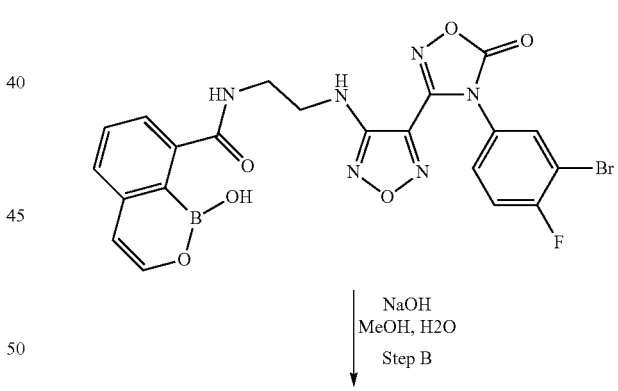

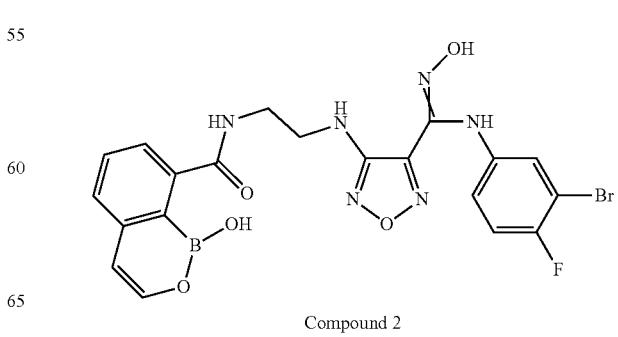

Compound 2

Example 2

Compound 2

N-(2-((4-(N-(3-Bromo-4-fluorophenyl)-N'-hydroxy-carbamimidoyl)-1,2,5-oxadiazol-3-yl)amino)ethyl)-1-hydroxy-1H-benzo[c][1,2]oxaborinine-8-carboxamide

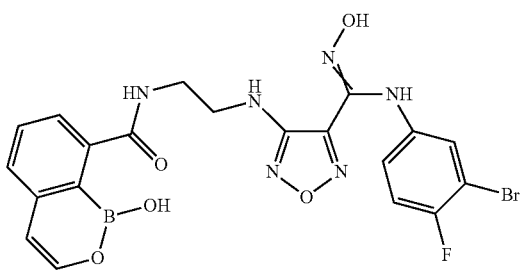

2

Step A

N-(2-((4-(4-(3-Bromo-4-fluorophenyl)-5-oxo-4,5-dihydro-1,2,4-oxadiazol-3-yl)-1,2,5-oxadiazol-3-yl)amino)ethyl)-1-hydroxy-1H-benzo[c][1,2]oxaborinine-8-carboxamide

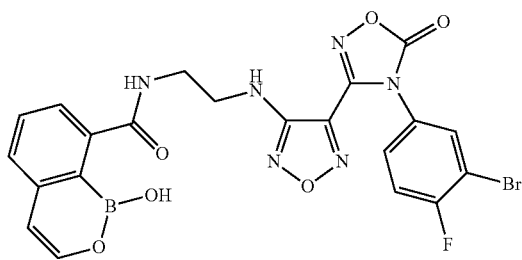 [SMILES: O=C(NCCNc1nonc1-c1noc(=O)n1-c1ccc(F)c(Br)c1)c1cccc2c1B(O)OC=C2]

A mixture of methyl 3-(2-methoxyvinyl)-2-(4,4,5,5-tetramethyl-1,3,2-dioxaborolan-2-yl)benzoate (43 mg, 0.136 mmol), 3-(4-((2-aminoethyl)amino)-1,2,5-oxadiazol-3-yl)-4-(3-bromo-4-fluorophenyl)-1,2,4-oxadiazol-5(4H)-one, hydrochloride, intermediate A (59 mg, 0.14 mmol), MeOH (2 mL), DIEA (0.105 g, 0.816 mmol) and DMAP (3.3 mg, 0.027 mmol) was heated to 80° C. for 5 h. The mixture was concentrated and the residue was dissolved in THF (2 mL) and 3N HCl/water (0.2 mL, 0.6 mmol) was added and the mixture was stirred at 50° C. for 1.5 h. The mixture was partitioned between EtOAc and water. The organic phase was dried ($Na_2SO_4$), concentrated and purified by reverse phase C18 HPLC (10-90% ACN/water, 0.05% TFA) to provide N-(2-((4-(4-(3-Bromo-4-fluorophenyl)-5-oxo-4,5-dihydro-1,2,4-oxadiazol-3-yl)-1,2,5-oxadiazol-3-yl)amino)ethyl)-1-hydroxy-1H-benzo[c][1,2]oxaborinine-8-carboxamide (34.3 mg, 45%) as an off-white solid. $^1$H NMR (400 MHz, DMSO-$d_6$) δ ppm 3.54 (dt, J=17.94, 5.33 Hz, 4 H) 6.41 (d, J=5.52 Hz, 1 H) 6.67 (t, J=5.65 Hz, 1 H) 7.20 (d, J=5.27 Hz, 1 H) 7.53-7.72 (m, 4 H) 7.73-7.80 (m, 1 H) 8.12 (dd, J=6.15, 2.38 Hz, 1 H) 8.85 (t, J=5.27 Hz, 1 H) 9.90 (br. s., 1 H). LC/MS (m/z) ES$^+$ : 557 (M+1)$^+$.

Step B

N-(2-((4-(N-(3-Bromo-4-fluorophenyl)-N'-hydroxy-carbamimidoyl)-1,2,5-oxadiazol-3-yl)amino)ethyl)-1-hydroxy-1H-benzo[c][1,2]oxaborinine-8-carboxamide

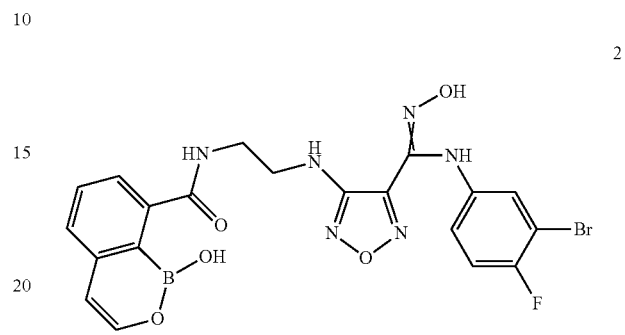

2

To a solution of N-(2-((4-(4-(3-bromo-4-fluorophenyl)-5-oxo-4,5-dihydro-1,2,4-oxadiazol-3-yl)-1,2,5-oxadiazol-3-yl)amino)ethyl)-1-hydroxy-1H-benzo[c][1,2]oxaborinine-8-carboxamide (32 mg, 0.055 mmol) in MeOH (0.5 mL) was added 1M NaOH/water (0.327 mL, 0.327 mmol) and the mixture was stirred at ambient temperature for 1 h. The mixture was purified by reverse phase C18 HPLC (10-90% ACN/water, 0.05% TFA) to provide N-(2-((4-(N-(3-bromo-4-fluorophenyl)-N'-hydroxycarbamimidoyl)-1,2,5-oxadiazol-3-yl)amino)ethyl)-1-hydroxy1H-benzo[c][1,2]oxaborinine-8-carboxamide (16.1 mg, 0.029 mmol, 53.3% yield) as an off-white solid. $^1$H NMR (400 MHz, DMSO-$d_6$) δ ppm 3.45-3.59 (m, 4 H) 6.31-6.44 (m, 2 H) 6.76 (dt, J=8.72, 3.42 Hz, 1 H) 7.07-7.23 (m, 3 H) 7.56 (dd, J=16.94, 7.40 Hz, 2 H) 7.63-7.73 (m, 1 H) 8.83-8.94 (m, 2 H) 9.85 (br. s., 1 H) 11.42 (s, 1 H). LC/MS (m/z) ES$^+$ : 531 (M+1)$^+$.

Scheme VI: Synthesis of Compound 3

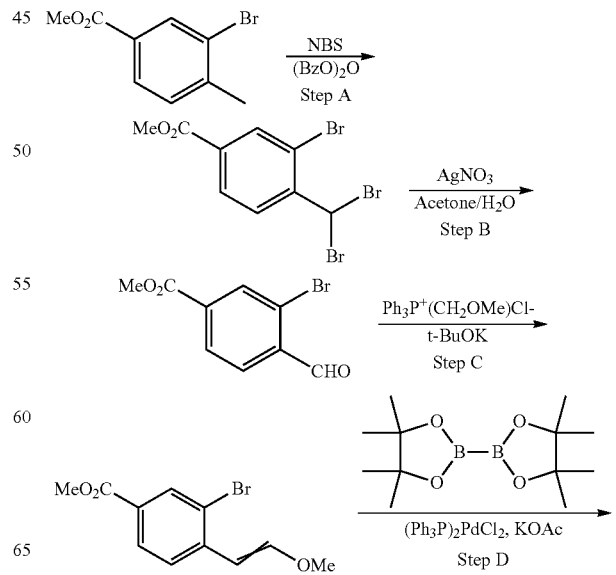

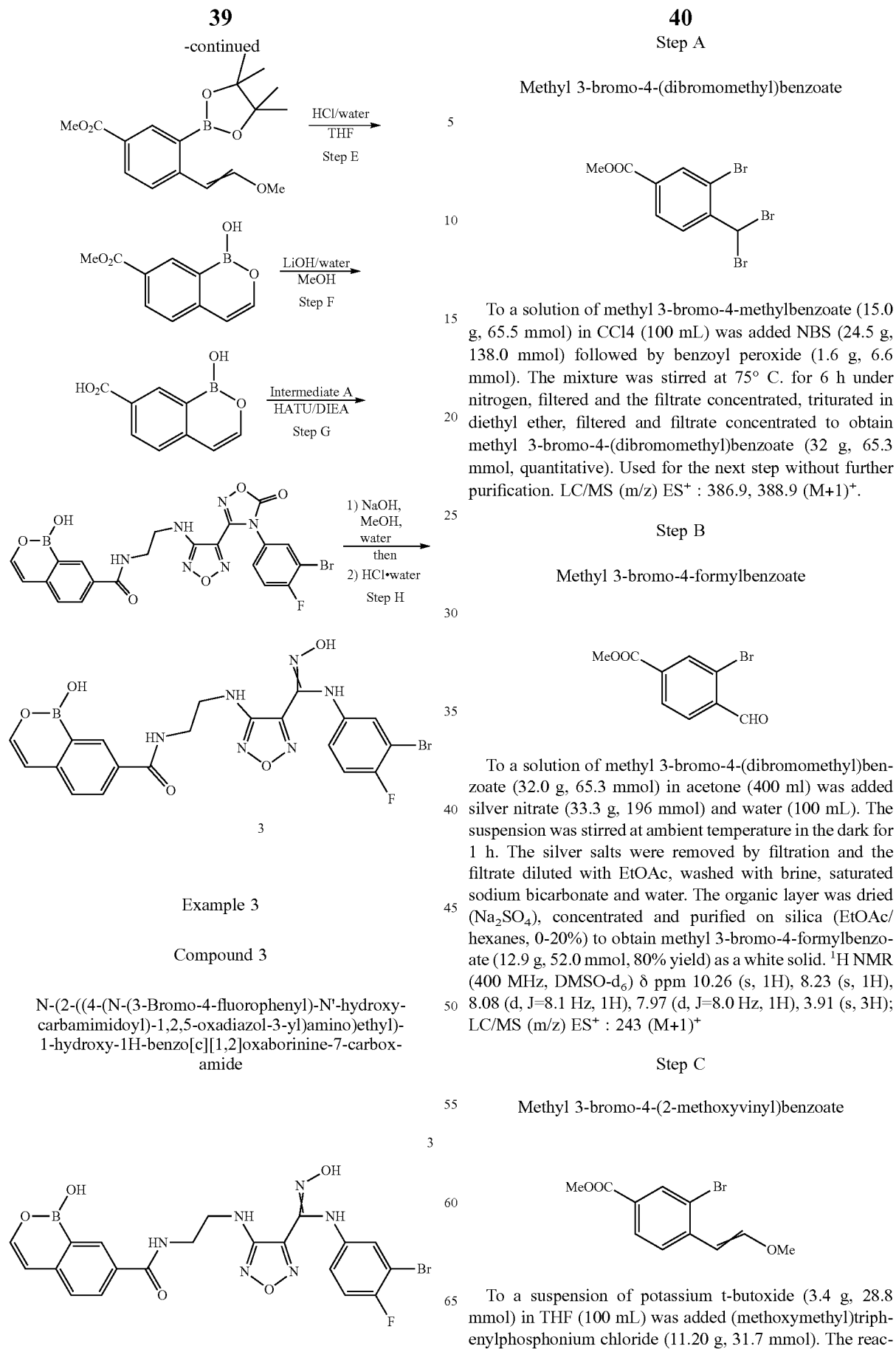

Example 3

Compound 3

N-(2-((4-(N-(3-Bromo-4-fluorophenyl)-N'-hydroxycarbamimidoyl)-1,2,5-oxadiazol-3-yl)amino)ethyl)-1-hydroxy-1H-benzo[c][1,2]oxaborinine-7-carboxamide

Step A

Methyl 3-bromo-4-(dibromomethyl)benzoate

To a solution of methyl 3-bromo-4-methylbenzoate (15.0 g, 65.5 mmol) in CCl4 (100 mL) was added NBS (24.5 g, 138.0 mmol) followed by benzoyl peroxide (1.6 g, 6.6 mmol). The mixture was stirred at 75° C. for 6 h under nitrogen, filtered and the filtrate concentrated, triturated in diethyl ether, filtered and filtrate concentrated to obtain methyl 3-bromo-4-(dibromomethyl)benzoate (32 g, 65.3 mmol, quantitative). Used for the next step without further purification. LC/MS (m/z) ES$^+$ : 386.9, 388.9 (M+1)$^+$.

Step B

Methyl 3-bromo-4-formylbenzoate

To a solution of methyl 3-bromo-4-(dibromomethyl)benzoate (32.0 g, 65.3 mmol) in acetone (400 ml) was added silver nitrate (33.3 g, 196 mmol) and water (100 mL). The suspension was stirred at ambient temperature in the dark for 1 h. The silver salts were removed by filtration and the filtrate diluted with EtOAc, washed with brine, saturated sodium bicarbonate and water. The organic layer was dried (Na$_2$SO$_4$), concentrated and purified on silica (EtOAc/hexanes, 0-20%) to obtain methyl 3-bromo-4-formylbenzoate (12.9 g, 52.0 mmol, 80% yield) as a white solid. $^1$H NMR (400 MHz, DMSO-d$_6$) δ ppm 10.26 (s, 1H), 8.23 (s, 1H), 8.08 (d, J=8.1 Hz, 1H), 7.97 (d, J=8.0 Hz, 1H), 3.91 (s, 3H); LC/MS (m/z) ES$^+$ : 243 (M+1)$^+$

Step C

Methyl 3-bromo-4-(2-methoxyvinyl)benzoate

To a suspension of potassium t-butoxide (3.4 g, 28.8 mmol) in THF (100 mL) was added (methoxymethyl)triphenylphosphonium chloride (11.20 g, 31.7 mmol). The reaction mixture was stirred at ambient temperature for 30 min, and the red solution was transferred into a closed flask containing methyl 3-bromo-4-formylbenzoate (3.5 g, 14.40 mmol) via a syringe and stirred at ambient temperature for 1 h. The reaction mixture was quenched with saturated ammonium chloride and partitioned between EtOAc and water. The aqueous layer was extracted again with EtOAc and the combined organic layers dried ($Na_2SO_4$), concentrated in vacuo and purified on silica (EtOAc/hexanes, 0-5%) to obtain methyl 3-bromo-4-(2-methoxyvinyl)benzoate (3.5 g, 12.26 mmol, 85% yield, mixture of E and Z isomers) as a white solid. LC/MS (m/z) $ES^+$ : 271 $(M+1)^+$.

Step D

Methyl 4-(2-methoxyyinyl)-3-(4,4,5,5-tetramethyl-1,3,2-dioxaborolan-2-yl)benzoate

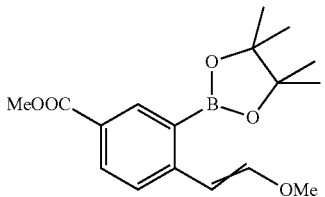 [SMILES: COC=Cc1ccc(C(=O)OC)cc1B1OC(C)(C)C(C)(C)O1]

To a mixture of methyl 3-bromo-4-(2-methoxyvinyl)benzoate (11.7 g, 43.2 mmol), bis(pinacolato)diboron (13.15 g, 51.8 mmol) and potassium acetate (12.71 g, 129 mmol) in 1,4-dioxane (200 mL) under $N_2$ was added bis(triphenylphosphine)palladium(II) chloride (3.03 g, 4.32 mmol) and the reaction stirred at 95° C. for 23 h. The reaction mixture was cooled and filtered. The filtrate was concentrated and purified on silica gel (EtOAc/hexanes, 0-5%) to obtain methyl 4-(2-methoxyvinyl)-3-(4,4,5,5-tetramethyl-1,3,2-dioxaborolan-2-yl)benzoate (11.72 g, 34.3 mmol, 79% yield, mixture of E and Z isomers). LC/MS (m/z) $ES^+$: 319 $(M+1)^+$.

Step E

Methyl 1-hydroxy-1H-benzo[c][1,2]oxaborinine-7-carboxylate

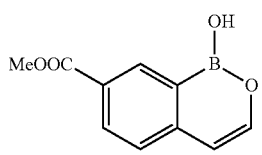

To a solution of methyl 4-(2-methoxyvinyl)-3-(4,4,5,5-tetramethyl-1,3,2-dioxaborolan-2-yl)benzoate (6.7 g, 21.06 mmol) in THF (211 mL) was added 4N HCl/water (52.6 mL, 211 mmol) and heated to 70° C. for 1.5 h. The mixture was partitioned between EtOAc and water. The organic layer was dried ($Na_2SO_4$), concentrated in vacuo and purified on silica (EtOAc/hexanes, 0-30%) to obtain methyl 1-hydroxy-1H-benzo[c][1,2]oxaborinine-7-carboxylate (2.86 g, 13.60 mmol, 64.6% yield) as a white solid. $^1$1-1 NMR (400 MHz, DMSO-$d_6$) δ ppm 9.51 (s, 1H), 8.66 (d, J=1.4 Hz, 1H), 8.12 (dd, J=1.8, 8.2 Hz, 1H), 7.54 (d, J=8.2 Hz, 1H), 7.28 (d, J=5.4 Hz, 1H), 6.44 (d, J=5.5 Hz, 1H), 3.32 (s, 3H). LC/MS (m/z) $ES^+$: 205 $(M+1)^+$.

Step F

1-Hydroxy-1H-benzo[c][1,2]oxaborinine-7-carboxylic acid

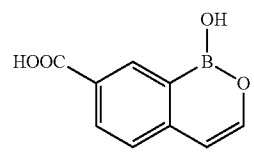

To a suspension of methyl 1-hydroxy-1H-benzo[c][1,2]oxaborinine-7-carboxylate (2.8 g, 13.73 mmol) in MeOH (100 mL) was added 1N lithium hydroxide/water (137 mL) and the mixture stirred at 50° C. for 2 h. Methanol was striped and the mixture acidified by adding concentrated HCl dropwise to form a white precipitate. The mixture was filtered and solid dried to obtain a white solid (1.6 g). The filtrate was extracted with EtOAc, dried ($Na_2SO_4$), and the solvent removed in vacuo to obtain another white solid (695 mg, 87% combined yield). $^1$H NMR (400 MHz, DMSO-$d_6$) δ ppm 12.91 (br, s, 1H), 9.45 (br, s, 1H), 8.65 (s, 1H), 8.10 (d, J=8.2 Hz, 1H), 7.51 (d, J=8.2 Hz, 1H), 7.26 (d, J=5.4 Hz, 1H), 6.43 (d, J=5.4 Hz, 1H). LC/MS (m/z) $ES^+$: 191 $(M+1)^+$.

Step G

N-(2-((4-(4-(3-Bromo-4-fluorophenyl)-5-oxo-4,5-dihydro-1,2,4-oxadiazol-3-yl)-1,2,5-oxadiazol-3-yl)amino)ethyl)-1-hydroxy-1H-benzo[c][1,2]oxaborinine-7-carboxamide

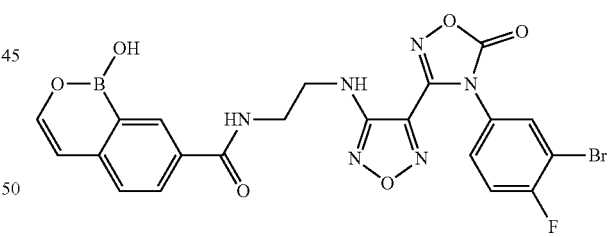

To 1-hydroxy-1H-benzo[c][1,2]oxaborinine-7-carboxylic acid (1.0 g, 5.26 mmol) in DMF (5 mL) was added HATU (2.202 g, 5.79 mmol) and DIEA (2.69 mL, 15.79 mmol) and the mixture stirred for 10 min followed by addition of 3-(4-((2-aminoethyl)amino)-1,2,5-oxadiazol-3-yl)-4-(3-bromo-4-fluorophenyl)-1,2,4-oxadiazol-5(4H)-one, Hydrochloride, intermediate A (2.219 g, 5.26 mmol). The mixture was stirred for 1 h, diluted with ethyl EtOAc and washed with 0.5N HCl and water. The organic layer was concentrate and dried in vacuo to obtain N-(2-((4-(4-(3-bromo-4-fluorophenyl)-5-oxo-4,5-dihydro-1,2,4-oxadiazol-3-yl)-1,2,5-oxadiazol-3-yl)amino)ethyl)-1-hydroxy-1H-benzo[c][1,2]oxaborinine-7-carboxamide (3.13 g, 5.62 mmol, quant). LC/MS (m/z) $ES^+$: 557 $(M+1)^+$

Step H

N-(2-((4-(N-(3-Bromo-4-fluorophenyl)-N'-hydroxy-carbamimidoyl)-1,2,5-oxadiazol-3-yl)amino)ethyl)-1-hydroxy-1H-benzo[c][1,2]oxaborinine-7-carboxamide

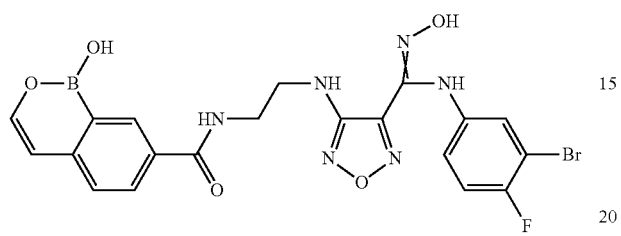

3

To a solution N-(2-((4-(4-(3-bromo-4-fluorophenyl)-5-oxo-4,5-dihydro-1,2,4-oxadiazol-3-yl)-1,2,5-oxadiazol-3-yl)amino)ethyl)-1-hydroxy-1H-benzo[c][1,2]oxaborinine-7-carboxamide (4.4 g, 7.90 mmol) in MeOH (40 mL) was added 1N NaOH/water (23.69 mL). The mixture was stirred at ambient temperature for 30 min. Methanol was removed and the mixture acidified with 1 N HCl (pH ~2) to form a precipitate that was filtered to obtain a yellow solid. The solid was purified reverse phase C18 HPLC (0-90% ACN/water, 0.05% TFA) to obtain a white solid (1.78 g, 3.07 mmol, 38.8% yield). $^1$H NMR (400 MHz, DMSO-$d_6$) δ ppm 11.42 (s, 1H), 9.35 (br, s, 1H), 8.88 (s, 1H), 8.67 (t, J=8.2Hz, 1H), 8.49 (s, 1H), 8.03 (dd, J=4 Hz, 8.2 Hz 1H), 7.48 (d, J=8.2 Hz, 1H), 7.22 (d, J=5.5 Hz, 1H), 7.13 (d, J=8.5 Hz, 2H), 6.80-6.68 (m, 1H), 6.40 (d, J=5.5 Hz, 1H), 6.34 (s, 1H), 3.50 (s, 2H), 3.46-3.41 (m, 2H). LC/MS (m/z) ES$^+$: 531 (M+1)$^+$.

Scheme VII: Synthesis of Compound 4

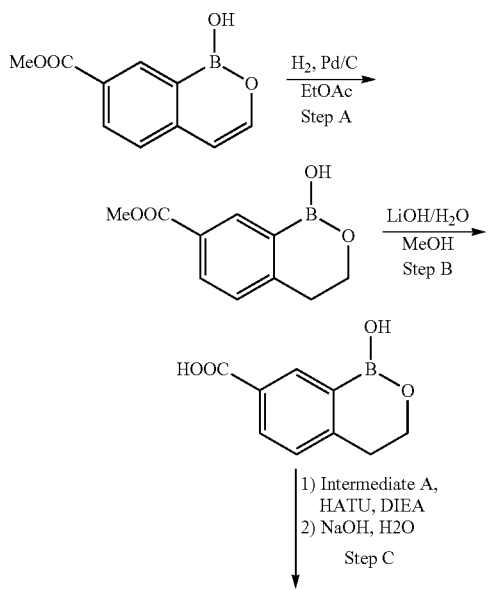

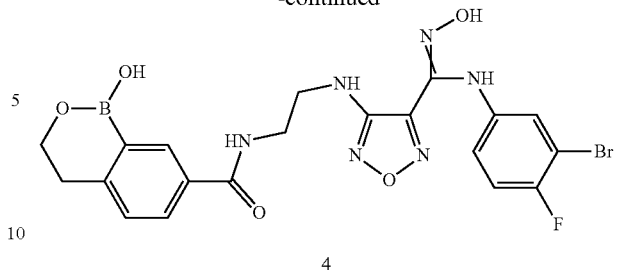

4

Example 4

Compound 4

N-(2-((4-(N-(3-Bromo-4-fluorophenyl)-N'-hydroxy-carbamimidoyl)-1,2,5-oxadiazol-3-yl)amino)ethyl)-1-hydroxy-3,4-dihydro-1H-benzo[c][1,2]oxaborinine-7-carboxamide

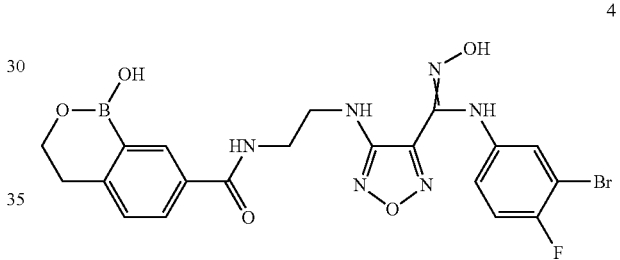

4

Step A

Methyl 1-hydroxy-3,4-dihydro-1H-benzo[c][1,2] oxaborinine-7-carboxylate

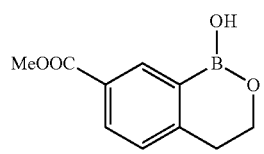 [SMILES: COC(=O)c1ccc2c(c1)B(O)OCC2]

To a solution of methyl 1-hydroxy-1H-benzo[c][1,2]oxaborinine-7-carboxylate (1.3 g, 6.37 mmol) in EtOAc (50 mL) was added 10% palladium on carbon (1.35 g, 1.27 mmol) and the mixture was stirred under hydrogen for 6 h. The mixture was filtered and the filtrate concentrated to obtain methyl 1-hydroxy-3,4-dihydro-1H-benzo[c][1,2]oxaborinine-7-carboxylate (1.03 g, 4.50 mmol, 70.6% yield) as a colorless oil. This was used for the next step without further purification. $^1$H NMR (400 MHz, CHLOROFORM-d) δ ppm 8.43 (d, J=1.6 Hz, 1H), 8.12-8.00 (m, 1H), 7.32-7.16 (m, 1H), 4.24 (t, J=6.0 Hz, 2H), 3.92 (s, 3H), 3.01 (t, J=6.0 Hz, 2H). LC/MS (m/z) ES$^+$: 207 (M+1)$^+$.

Step B

1-Hydroxy-3,4-dihydro-1H-benzo[c][1,2]oxaborinine-7-carboxylic acid

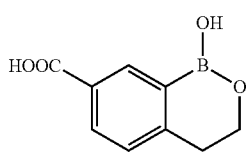 [SMILES: O=C(O)c1ccc2c(c1)B(O)OCC2]

To a suspension of methyl 1-hydroxy-3,4-dihydro-1H-benzo[c][1,2]oxaborinine-7-carboxylate (1 g, 4.85 mmol) in MeOH (50 mL) was added 1N lithium hydroxide/water (49.5 mL). Methanol was removed in vacuo and 1N HCl/water added to pH ~1. Precipitate formed filtered to obtain white solid (460 mg). The filtrate was extracted with EtOAc, dried (Na$_2$SO$_4$) and the solvent removed in vacuo to obtain another 270 mg of the white solid (64% combined yield). $^1$H NMR (400 MHz, DMSO-d$_6$) δ ppm 12.82 (br, s, 1H) 8.63 (s, 1H), 8.29 (s, 1H), 7.94 (d, J=7.8 Hz, 1H), 7.33 (d, J=7.8 Hz, 1H), 4.09 (t, J=6.0 Hz, 2H), 2.93 (t, J=6.0 Hz, 2H). LC/MS (m/z) ES$^+$: 193 (M+1)$^+$.

Step C

N-(2-((4-(N-(3-Bromo-4-fluorophenyl)-N'-hydroxycarbamimidoyl)-1,2,5-oxadiazol-3-yl)amino)ethyl)-1-hydroxy-3,4-dihydro-1H-benzo[c][1,2]oxaborinine-7-carboxamide

4

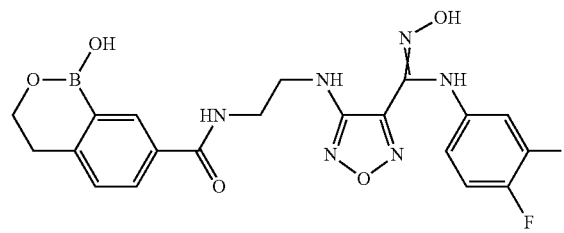

To 1-hydroxy-3,4-dihydro-1H-benzo[c][1,2]oxaborinine-7-carboxylic acid (101 mg, 0.474 mmol) in DMF (5 mL) was added HATU (198 mg, 0.522 mmol) and DIEA (0.242 mL, 1.423 mmol). The mixture was stirred for 10 min followed by addition of 3-(4-((2-aminoethyl)amino)-1,2,5-oxadiazol-3-yl)-4-(3-bromo-4-fluorophenyl)-1,2,4-oxadiazol-5(4H)-one, hydrochloride, intermediate A (200 mg, 0.474 mmol) and stirred for 20 min. 1 N NaOH/water (2 mL) was added and stirring continued for 2 h. The mixture was purified reverse phase C18 HPLC (0-90% ACN/water, 0.05% TFA) to obtain a white solid (88 mg, 0.136 mmol, 28.7% yield). $^1$H NMR (400 MHz, DMSO-d$_6$) δ ppm 11.43 (s, 1H), 8.88 (s, 1H), 8.59 (t, J=7.9 Hz, 2H), 8.16 (s, 1H), 7.85 (d, J=7.9 Hz, 1H), 7.29 (d, J=8.0 Hz, 1H), 7.18-7.09 (m, 2H), 6.80-6.70 (m, 1H), 6.32 (s, 1H), 4.08 (t, J=6.0 Hz, 2H), 3.42 (br. s., 3H), 2.91 ((t, J=6.0 Hz, 2H). LC/MS (m/z) ES$^+$: 533 (M+1)$^+$.

Scheme VIII: Synthesis of Compound 5

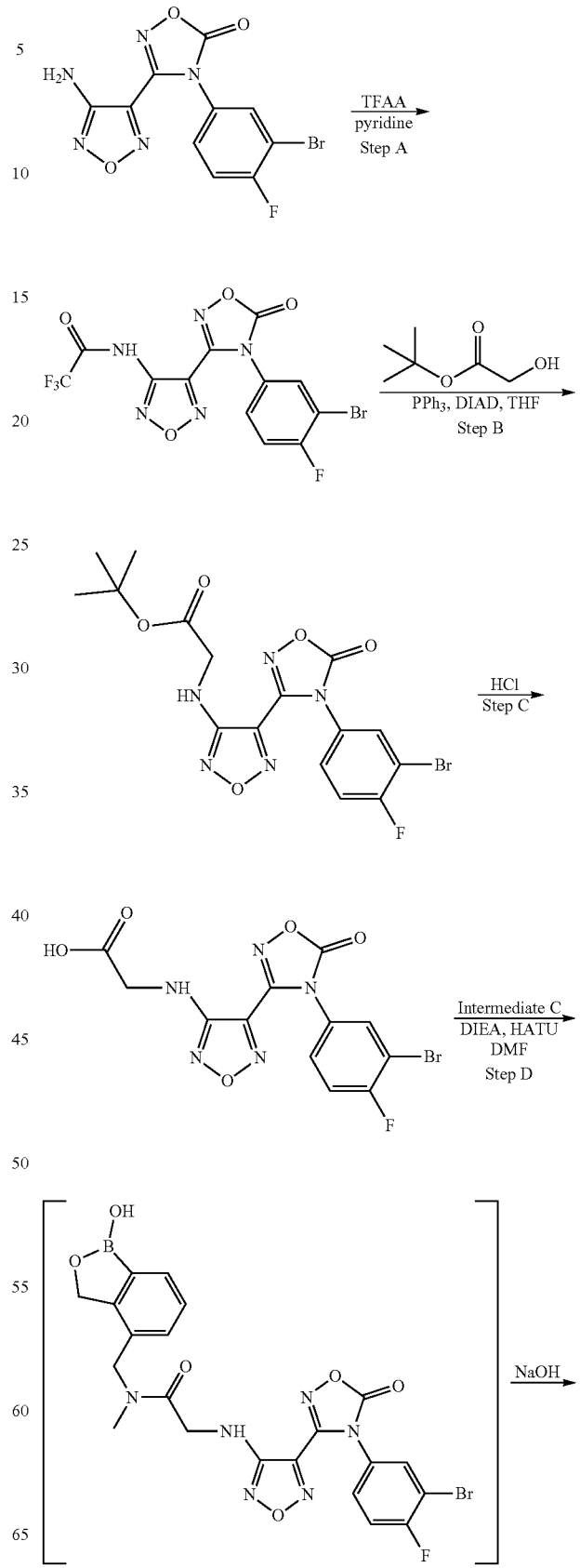

-continued

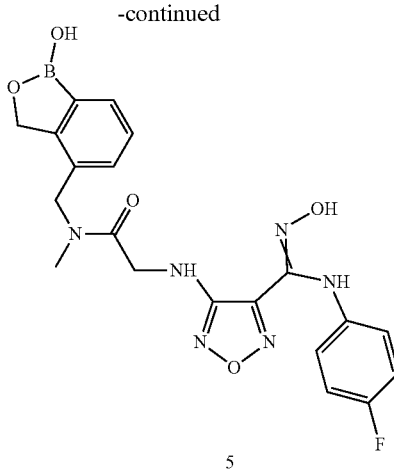

Example 5

Compound 5

2-((4-(N-(3-Bromo-4-fluorophenyl)-N'-hydroxycar-bamimidoyl)-1,2,5-oxadiazol-3-yl)amino)-N-((1-hydroxy-1,3-dihydrobenzo[c][1,2]oxaborol-4-yl)methyl)-N-methylacetamide 2,2,2-trifluoroacetate

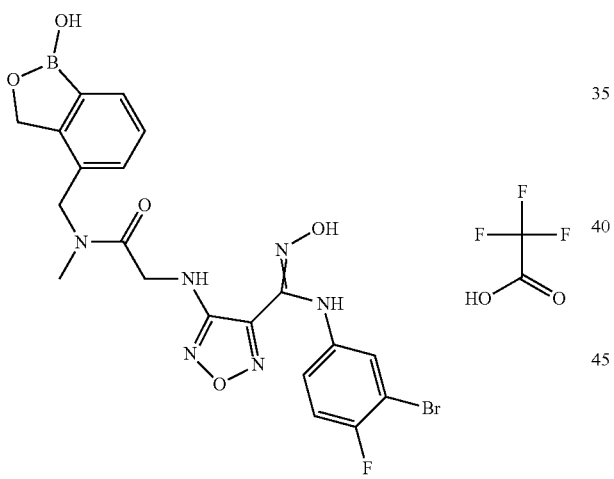

Step A

N-(4-(4-(3-Bromo-4-fluorophenyl)-5-oxo-4,5-dihydro-1,2,4-oxadiazol-3-yl)-1,2,5-oxadiazol-3-yl)-2,2,2-trifluoroacetamide

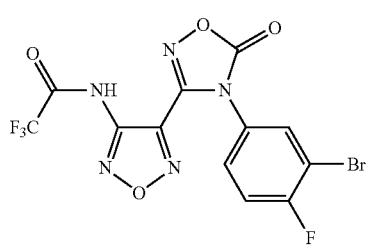 [SMILES: O=C(Nc1nonc1-c1noc(=O)n1-c1ccc(F)c(Br)c1)C(F)(F)F]

A solution of 3-(4-amino-1,2,5-oxadiazol-3-yl)-4-(3-bromo-4-fluorophenyl)-1,2,4-oxadiazol-5(4H)-one (1.026 g, 3.00 mmol) in DCM (12 mL) at 0° C. was treated with 2,2,2-trifluoroacetic anhydride (0.834 mL, 6.00 mmol) and pyridine (0.485 mL, 6.00 mmol). The reaction mixture was stirred at room temperature for 10 min. The reaction mixture was then cooled to 0° C. and was quenched with water (2 mL), diluted with EtOAc (30 mL) and the layers were separated. The organics were was washed with 1M HCl solution (10 mL), water (2×10 mL), brine (10 mL), and dried over Na$_2$SO$_4$. Silica gel (2 g) was added and the solvent was evaporated to obtain a silica gel plug. The product was purified by silica gel chromatography (10% and 20% EtOAc/hexane) to obtain N-(4-(4-(3-bromo-4-fluorophenyl)-5-oxo-4,5-dihydro-1,2,4-oxadiazol-3-yl)-1,2,5-oxadiazol-3-yl)-2,2,2-trifluoroacetamide (1.14 g, 2.52 mmol, 84% yield) as a white solid. $^1$H NMR (400 MHz, DMSO-d$_6$) δ7.94-7.89 (m, 1H), 7.56-7.51 (m, 2H). LC/MS (m/z) ES$^-$: 436.2, 438.2 (M−1)$^-$.

Step B tert-Butyl 2-((4-(4-(3-bromo-4-fluorophenyl)-5-oxo-4,5-dihydro-1,2,4-oxadiazol-3-yl)-1,2,5-oxadiazol-3-yl)amino)acetate

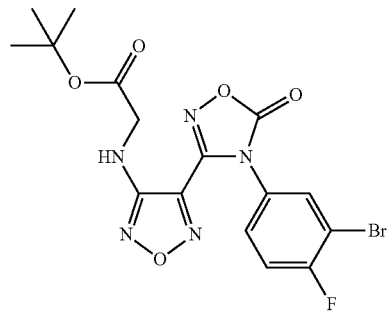 [SMILES: CC(C)(C)OC(=O)CNc1nonc1-c1noc(=O)n1-c1ccc(F)c(Br)c1]

A solution of triphenylphosphine (1527 mg, 5.82 mmol), tert-butyl 2-hydroxyacetate (769 mg, 5.82 mmol), and N-(4-(4-(3-bromo-4-fluorophenyl)-5-oxo-4,5-dihydro-1,2,4-oxadiazol-3-yl)-1,2,5-oxadiazol-3-yl)-2,2,2-trifluoroacetamide (850 mg, 1.940 mmol) in THF (8 mL) was cooled to 0° C. and treated with (E)-diisopropyl diazene-1,2-dicarboxylate (1.146 mL, 5.82 mmol). The reaction was stirred at room temperature for 24 h. Silica gel (5 g) was added and the solvent was evaporated. The silica gel plug was purified using silica gel chromatography (20% EtOAc/hexane) to give a semi-solid residue. MeOH was added to afford tert-butyl 2-((4-(4-(3-bromo-4-fluorophenyl)-5-oxo-4,5-dihydro-1,2,4-oxadiazol-3-yl)-1,2,5-oxadiazol-3-yl)amino) acetate (445 mg, 0.925 mmol, 47.7% yield) as white crystals. $^1$H NMR (400 MHz, DMSO-d6) δ 8.12 (dd, J=2.5, 6.2 Hz, 1H), 7.75 (ddd, J=2.5, 4.4, 8.8 Hz, 1H), 7.64-7.57 (m, 1H), 6.83 (t, J=6.2 Hz, 1H), 3.95 (d, J=6.2 Hz, 2H), 1.41 (s, 9H). LC/MS (m/z) ES$^-$: 454.2, 456.2 (M−1)$^-$.

Step C 2-((4-(4-(3-Bromo-4-fluorophenyl)-5-oxo-4,5-dihydro-1,2,4-oxadiazol-3-yl)-1,2,5-oxadiazol-3-yl)amino)acetic acid

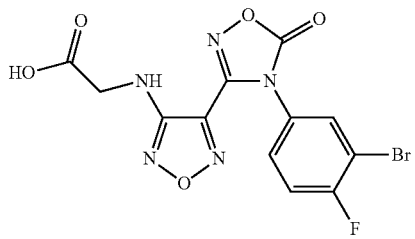 [SMILES: O=C(O)CNc1nonc1-c1noc(=O)n1-c1ccc(F)c(Br)c1]

tert-Butyl 2-((4-(4-(3-bromo-4-fluorophenyl)-5-oxo-4,5-dihydro-1,2,4-oxadiazol-3-yl)-1,2,5-oxadiazol-3-yl)amino)acetate (550 mg, 1.206 mmol) was dissolved in THF (10 mL) and treated with HCl, 4M in dioxanes (6.03 mL, 24.11 mmol). The reaction was stirred at room temperature for 17 hours. The reaction was treated with additional HCl, 4M in dioxanes (6.03 mL, 24.1 mmol) and stirred at room temperature for an additional 22 hours. The reaction was treated with additional HCl, 4M in dioxanes (6.03 mL, 24.1 mmol) and stirred at room temperature for 4 hr then refrigerated for 48 hours. The reaction was returned to room temperature and treated with additional HCl, 4M in dioxanes (4 mL) and stirred for an additional 8 hours. The solvents were then evaporated to give a oil that was dissolved in MeOH and purified using reverse phase chromatography (ACN/water 10-90%, 0.05% TFA, 20 min) to provide 2-((4-(4-(3-bromo-4-fluorophenyl)-5-oxo-4,5-dihydro-1,2,4-oxadiazol-3-yl)-1,2,5-oxadiazol-3-yl)amino)acetic acid (170 mg, 0.425 mmol, 35.2% yield) as a white solid. $^1$H NMR (400 MHz, DMSO-$d_6$) δ 12.73-13.40 (1 H, m), 8.12 (dd, J=2.5, 6.2 Hz, 1H), 7.76 (td, J=2.2, 4.4 Hz, 1H), 7.63-7.57 (m, 1H), 6.79 (t, J=6.1 Hz, 1H), 3.98 (d, J=6.1 Hz, 2H). LC/MS (m/z) ES$^-$: 398.1, 400.2 (M−1)$^-$.

Step D 2-((4-(N-(3-Bromo-4-fluorophenyl)-N'-hydroxycarbamimidoyl)-1,2,5-oxadiazol-3-yl)amino)-N-((1-hydroxy-1,3-dihydrobenzo[c][1,2]oxaborol-4-0methyl)-N-methylacetamide 2,2,2-trifluoroacetate

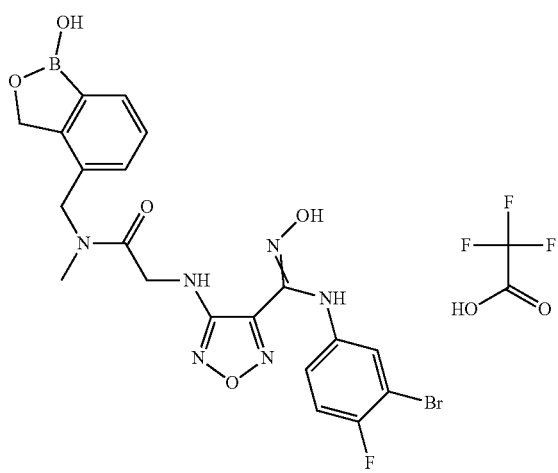

A solution of 2-((4-(4-(3-bromo-4-fluorophenyl)-5-oxo-4,5-dihydro-1,2,4-oxadiazol-3-yl)-1,2,5-oxadiazol-3-yl)amino)acetic acid(50 mg, 0.125 mmol) and 4-((methylamino)methyl)benzo[c][1,2]oxaborol-1(3H)-ol, hydrochloride, intermediate C (53.4 mg, 0.250 mmol) in DMF (1 mL) was treated with N-ethyl-N-isopropylpropan-2-amine (0.109 mL, 0.625 mmol) and HATU (52.3 mg, 0.137 mmol). The mixture was stirred at room temperature for 30 minutes. The reaction, when then treated with 1N NaOH (0.7 mL) and stirred at room temperature for 1.5 hours. The reaction was then treated with 1N NaOH (0.7 mL) and stirred for 1 hour. The reaction mixture was purified using reverse phase chromatography (ACN/water 10-90%, 0.05% TFA, 20 min) to provide 2-((4-(N-(3-bromo-4-fluorophenyl)-N'-hydroxycarbamimidoyl)-1,2,5-oxadiazol-3-yl)amino)-N-((1-hydroxy-1,3-dihydrobenzo[c][1,2]oxaborol-4-yl)methyl)-N-methylacetamide, 0.5 trifluoroacetic acid salt (44 mg, 0.074 mmol, 59.1% yield) as a white solid. $^1$H NMR (two sets of signals due to cis/trans amide) (400 MHz, METHANOL-d4) δ 7.61 (d, J=4.3 Hz, 1H (two sets)), 7.43-7.27 (m, 2H (two sets)), 7.16 (dd, J=2.7, 5.9 Hz, 1H (two sets)), 7.08-7.01(m, 1H (two sets)), 6.91-6.83 (m, 1H (two sets)), 5.13 and 5.07 (s, 0.50-F1.50H), 4.67 and 4.63 (s, 1.5+0.5H), 4.25 and 4.21 (s, 1.5+0.5H), 2.98 (s, 3H). LC/MS (m/z) ES$^+$: 533.3, 535.2 (M+1)$^+$.

Example 6

Compound 6

N-(2-((4-(N-(3-Bromo-4-fluorophenyl)-N'-hydroxycarbamimidoyl)-1,2,5-oxadiazol-3-yl)amino)ethyl)-1-hydroxy-1,3-dihydrobenzo[c][1,2]oxaborole-7-carboxamide

6

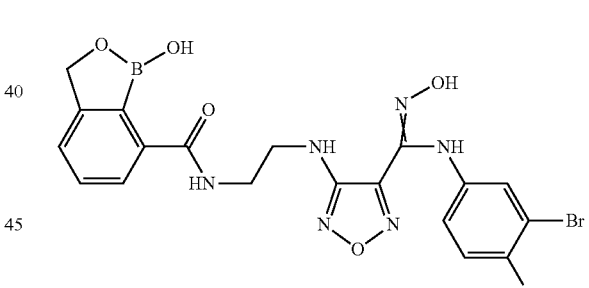

A solution of 1-hydroxy-1,3-dihydrobenzo[c][1,2]oxaborole-7-carboxylic acid, intermediate B (295 mg, 1.660 mmol), intermediate B and 3-(4-((2-aminoethyl)amino)-1,2,5-oxadiazol-3-yl)-4-(3-bromo-4-fluorophenyl)-1,2,4-oxadiazol-5(4H)-one, hydrochloride, intermediate A (700 mg, 1.660 mmol) in DMF (10 mL) was treated with DIPEA (0.870 mL, 4.98 mmol) followed by HATU (694 mg, 1.826 mmol). The reaction mixture was stirred at room temperature for 45 minutes. The reaction was then treated by the slow dropwise addition of 1N NaOH (5 mL) and then stirred for 40 minutes. The reaction was then treated with 1N NaOH (2 mL) and stirred for 1.5 hours. The reaction was kept in the refrigerator overnight and taken and treated with additional 1N NaOH (5 mL) and stirred for 3.5 hours. The reaction mixture was purified using reverse phase chromatography (ACN/water 10-90%, 0.05% TFA, 15 min) to provide N-(2-((4-(N-(3-bromo-4-fluorophenyl)-N'-hydroxycarbamimidoyl)-1,2,5-oxadiazol-3-yl)amino)ethyl)-1-hydroxy-1,3-dihydrobenzo[c][1,2]oxaborole-7-carboxamide, 0.2 trifluoroacetic acid salt (380 mg, 0.680 mmol, 41.0% yield) as a white solid. $^1$H NMR (400 MHz, MeOH-d$_4$) δ 7.90 (d, J=7.7 Hz, 1H), 7.66-7.49 (m, 2H), 7.15-6.96 (m, 2H), 6.86-6.77 (m, 1H), 4.98 (br. s., 2H), 3.83-3.75 (m, 2H), 3.61 (d, J=6.0 Hz, 2H). LC/MS (m/z) ES$^+$: 519.2, 521.2 (M+1)$^+$.

Administration and Formulation

In another embodiment, there is provided a pharmaceutical composition comprising a pharmaceutically acceptable diluent and a therapeutically effective amount of a compound of Formulas I-VII or a pharmaceutically acceptable salt thereof.

The compounds of the present invention can be supplied in the form of a pharmaceutically acceptable salt. The terms "pharmaceutically acceptable salt" refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to Formulas I-VII may be prepared. These pharmaceutically acceptable salts may be prepared in situ during the final isolation and purification of the compound, or by separately reacting the purified compound in its free acid or free base form with a suitable base or acid, respectively.

Illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitic, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. Preferred pharmaceutically acceptable salts include the salts of hydrochloric acid and trifluoroacetic acid.

Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, Na$_2$CO$_3$, K$_2$CO$_3$, NaH, and potassium-t-butoxide.

Salts derived from pharmaceutically acceptable organic non-toxic bases include salts of primary, secondary, and tertiary amines, including in part, trimethylamine, diethylamine, N, N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences*, 17th ed., Mack Publishing Company, Easton, Pa., 1985, p. 1418, the disclosure of which is hereby incorporated by reference only with regards to the lists of suitable salts.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. D$_2$O, d$_6$-acetone, d$_6$-DMSO.

Compounds of Formulas 1-VII containing one or more asymmetric carbon atoms can exist as two or more stereoisomers. Where a compound of Formulas I-VII contains an amidoxime or alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope in some embodiments or alternate embodiements of the claimed compounds in the present invention are all stereoisomers, geometric isomers and tautomeric forms of the compounds of Formulas I-VII, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where in some embodiments or alternate embodiments the compounds of Formulas I-VII contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of Formulas I-VII wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formulas I-VII, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labelled compounds of Formulas I-VII can generally be prepared by conventional techniques known to those skilled in the art or by processes analogous to those described in the accompanying Examples and Preparations using an appropriate isotopically-labelled reagent& in place of the non-labelled reagent previously employed.

The compounds of the present invention may be administered as prodrugs. Thus, certain derivatives of compounds of Formulas I-VII, which may have little or no pharmacological activity themselves can, when administered into or onto the body, be converted into compounds of Formula I as 'prodrugs'.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see Remington's Pharmaceutical Sciences, Mack Publishing Company, Easton, Pa.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used the route and form of administration, and other factors. The drug can be administered more than once a day, such as once or twice a day.

Therapeutically effective amounts of the chemical entities described herein may range from approximately 0.01 to 200 mg per kilogram body weight of the recipient per day; such as about 0.01-100 mg/kg/day, for example, from about 0.1 to 50 mg/kg/day. Thus, for administration to a 70 kg person, the dosage range may be about 7-3500 mg per day.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MD's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %.

Compound Data

Human indoleamine 2,3-dioxgenase (IDO) enzyme and cellular data, and rat and mouse clearance data are presented in Table 2 below. FIG. 1 shows the rat oral pharmacokinetic (PK) as drug concentration vs. time. Brief descriptions of the enzyme and cellular assays and of in vivo pharmacokinetic methods for rat are below, following the table and graphs.

TABLE 2

| Compound | pXC$_{50}$ | | | | Clearance [mL/min/kg] | |
| --- | --- | --- | --- | --- | --- | --- |
| | enzyme | HeLa | PBMC | MDDC | rat | mouse |
| 1 | 7.0 | 7.0 | 6.9 | 6.8 | 0.8 | 0.6 |
| 2 | 6.7 | 6.2 | 6.3 | n/a | n.d | n.d |
| 3 | 7.1 | 5.9 | 6.5 | 5.7 | 0.8 | n.d. |
| 4 | 7.3 | 6.8 | 7.0 | 5.9 | 2.0 | n.d |
| 5 | 7.0 | 6.7 | 6.8 | 6.9 | 2.8 | 3.1 |
| 6 | 7.1 | 6.8 | 7.0 | 7.0 | 4.8 | 7.1 |
| 7 | 7.0 | 6.2 | 6.4 | n/a | 180.0 | n/a |
| 8 | 7.1 | 6.8 | 7.3 | 7.1 | 74.9 | n/a |
| 9 | 7.5 | 7.0 | 7.5 | 7.2 | 238.5 | n/a |
| 10 | 7.6 | 6.8 | 6.7 | 6.2 | 220.0 | n/a |
| 11 | 7.1 | 7.8 | 7.7 | 7.1 | 50.6 | 37.2 |

Compounds 7, 8, 9, and 10, structures below, were made internally. The synthesis are not provided here, but can be prepared in a variety of ways know to one skilled in the art of organic synthesis. Taken together they serve to illustrate not all IDO active compounds have good rat clearance.

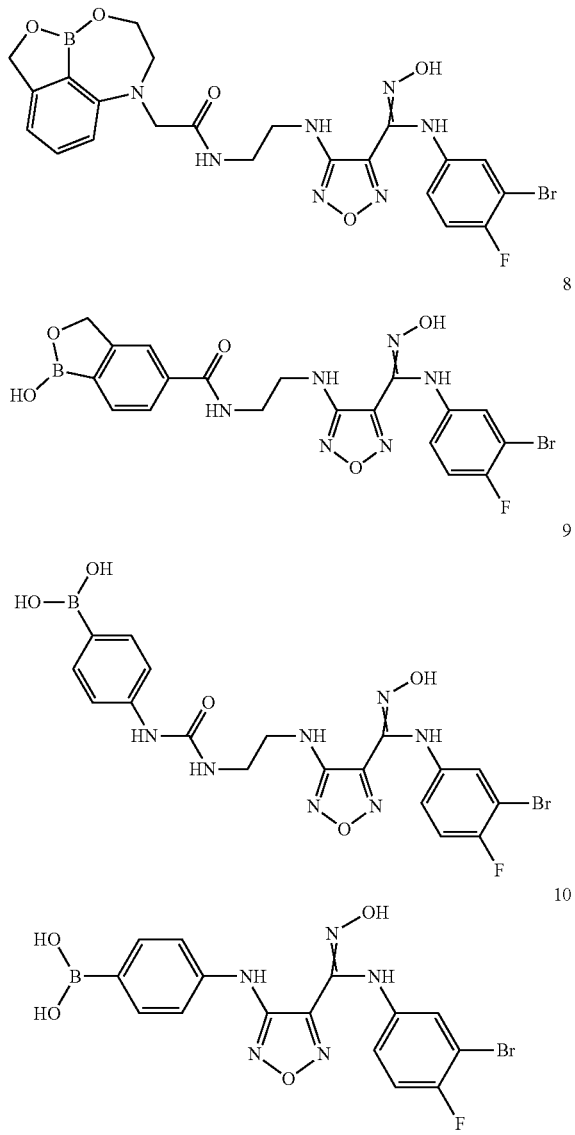

Compounds 11 has the structure below and is referenced in WO 2010/005958.

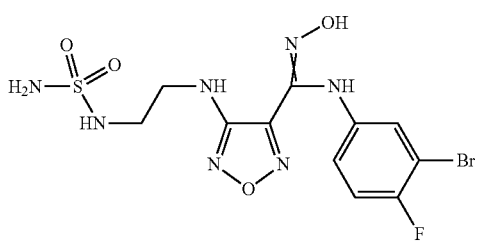

IDOi enzyme assay: Compounds of the present invention were tested against indoleamine 2,3 dioxygenase (IDO1) in an absorbance readout assay. IDO1 catalyzes tryptophan oxidation using L- or D-tryptophan and molecular oxygen as substrates to form N-formylkynurenine (NFK). NFK has an absorbance peak near 320 nm, which allows the reaction progress to be monitored spectrophotometrically via absorbance increase at 320 nm. Inhibition of the increase in absorbance observed with NFK product formation is interpreted as inhibition of IDO1 activity. Recombinant human IDO1 that had been expressed in *E. coli* was used for these experiments.

In preparation for the assay, test compounds were serially diluted 3-fold in DMSO from a typical top concentration of 5 mM and plated at 0.5 µL in 384-well, UV-Star, flat bottom plates (Greiner Bio-One, Kremsmünster, Austria) to generate 11-point dose response curves. Low control wells (100% inhibition, 0% NFK) contained 0.5 µL of DMSO in the absence of IDO1, and high control wells (0% inhibition, 100% NFK) contained 0.5 µL of DMSO in the presence of the enzyme.

To begin the assay, 25 µL of a 2×enzyme solution with a composition of 100 mM potassium phosphate (pH 7.2), 1 mM CHAPS, 40 mM L-ascorbic acid, 2 µM methylene blue, 1% v/v catalase (Sigma-Aldrich, St. Louis, Mo.) and 100 nM IDO1 were added to all wells of the 384-well compound plates, with the exception of the low control wells. The low control wells received 25 µL of a similar 2×solution lacking the IDO1 enzyme. Before addition of substrate to the plates, the enzyme solution and compounds were allowed to pre-incubate at room temperature for 30 minutes.

Following preincubation, 25 µL of a 2×substrate solution with a composition of 100 mM potassium phosphate (pH 7.2), 1 mM CHAPS, and 4 mM D-tryptophan (Sigma-Aldrich, St. Louis, Mo.) were added to all wells of the 384-well compound plates. The final assay composition in the plate was 100 mM potassium phosphate (pH 7.2), 1 mM CHAPS, 20 mM L-ascorbic acid, 1 µM methylene blue, 0.5% v/v catalase, +/−50 nM IDO1, and 2 mM D-tryptophan.

Two absorbance reads at 320 nm were captured for each well using the EnVision® Multilabel Reader (PerkinElmer Inc., Waltham, Mass.). The first read was acquired at 5 minutes following addition of the 2×substrate solution, and the second read was acquired 55 minutes later. For data analysis purposes, the initial read is subtracted from the second read to account for wells with high absorbance backgrounds due to test compound absorbance.

The data for dose responses were plotted as % IDO1 inhibition versus compound concentration following normalization using the formula $100-(100*((U-C2)/(C1-C2)))$, where U was the unknown value, C1 was the average of the high (100% NFK; 0% inhibition) control wells and C2 was the average of the low (0% NFK; 100% inhibition) control wells.

Curve fitting was performed with the equation $y=A+((B-A)/(1+(10^X/10^C)^D))$, where A was the minimum response, B was the maximum response, C was the log ($XC_{50}$) and D was the Hill slope. The results for each test compound were recorded as pIC50 values (−C in the above equation).

HeLa IDOi assay: Compounds of the present invention were tested via high-throughput cellular assays utilizing detection of kynurenine via mass spectrometry and cytotoxicity as end-points. For the mass spectrometry and cytotoxicity assays, human epithelial HeLa cells (CCL-2; ATCC®, Manassas, Va.) were stimulated with human interferon-γ (IFN-γ) (Sigma-Aldrich Corporation, St. Louis, Mo.) to induce the expression of indoleamine 2, 3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 5 mM and plated at 0.5 µL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 µL of DMSO in the presence of unstimulated (−IFN-γ) HeLa cells for the mass spectrometry assay or 0.5 µL of DMSO in the absence of cells for the cytotoxicity assay, and high control wells (100% kynurenine or 0% cytotoxicity) contained 0.5 µL of DMSO in the presence of stimulated (+IFN-γ) HeLa cells for both the mass spectrometry and cytotoxicity assays.

Frozen stocks of HeLa cells were washed and recovered in DMEM high glucose medium with HEPES (Thermo Fisher Scientific, Inc., Waltham, Mass.) supplemented with 10% v/v certified fetal bovine serum (FBS) (Thermo Fisher Scientific, Inc., Waltham, Mass.), and 1×penicillin-streptomycin antibiotic solution (Thermo Fisher Scientific, Inc., Waltham, Mass.). The cells were diluted to 100,000 cells/mL in the supplemented DMEM medium. 50 µL of either the cell suspension, for the mass spectrometry assay, or medium alone, for the cytotoxicity assay, were added to the low control wells, on the previously prepared 384-well compound plates, resulting in 5,000 cells/well or O cells/well respectively. IFN-γ was added to the remaining cell suspension at a final concentration of 10 nM, and 50 µL of the stimulated cells were added to all remaining wells on the 384-well compound plates. The plates, with lids, were then placed in a 37° C., 5% $CO_2$ humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 10 µL were added to each plate well. After a twenty minute incubation at room temperature, luminescence was read on an EnVision® Multilabel Reader (PerkinElmer Inc., Waltham, Mass.). For the mass spectrometry assay, 10 µL of supernatant from each well of the compound-treated plates were added to 40 µL of acetonitrile, containing 10 µM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 µL from each well of the acetonitrile extraction plates were added to 90 µL of sterile, distilled $H_2O$ in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as % IDO1 inhibition versus compound concentration following normalization using the formula 100−(100*((U−C2)/(C1−C2))), where U was the unknown value, C1 was the average of the high (100% kynurenine; 0% inhibition) control wells and C2 was the average of the low (0% kynurenine; 100% inhibition) control wells. The data for dose responses in the cytotoxicity assay were plotted as % cytotoxicity versus compound concentration following normalization using the formula 100−(100*((U−C2)/(C1−C2))), where U was the unknown value, C1 was the average of the high (0% cytotoxicity) control wells and C2 was the average of the low (100% cytotoxicity) control wells.

Curve fitting was performed with the equation))y=A+((B−A)/(1+($10^X/10^C)^D$)), where A was the minimum response, B was the maximum response, C was the log ($XC_{50}$) and D was the Hill slope. The results for each test compound were recorded as pIC50 values for the mass spectrometry assay and as pCC50 values for the cytotoxicity assay (−C in the above equation).

PBMC IDOi assay: Compounds of the present invention were tested via high-throughput cellular assays utilizing detection of kynurenine via mass spectrometry and cytotoxicity as end-points. For the mass spectrometry and cytotoxicity assays, human peripheral blood mononuclear cells (PBMC) (PB003F; AllCells®, Alameda, Calif.) were stimulated with human interferon-γ (IFN-γ) (Sigma-Aldrich Corporation, St. Louis, Mo.) and lipopolysaccharide from *Salmonella minnesota* (LPS) (Invivogen, San Diego, Calif.) to induce the expression of indoleamine 2, 3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 5 mM and plated at 0.5 µL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 µL of DMSO in the presence of unstimulated (−IFN-γ/−LPS) PBMCs for the mass spectrometry assay or 0.5 µL of DMSO in the absence of cells for the cytotoxicity assay, and high control wells (100% kynurenine or 0% cytotoxicity) contained 0.5 µL of DMSO in the presence of stimulated (+IFN-γ/+LPS) PBMCs for both the mass spectrometry and cytotoxicity assays.

Frozen stocks of PBMCs were washed and recovered in RPMI 1640 medium (Thermo Fisher Scientific, Inc., Waltham, Mass.) supplemented with 10% v/v heat-inactivated fetal bovine serum (FBS) (Thermo Fisher Scientific, Inc., Waltham, Mass.), and 1×penicillin-streptomycin antibiotic solution (Thermo Fisher Scientific, Inc., Waltham, Mass.). The cells were diluted to 1,000,000 cells/mL in the supplemented RPMI 1640 medium. 50 µL of either the cell suspension, for the mass spectrometry assay, or medium alone, for the cytotoxicity assay, were added to the low control wells, on the previously prepared 384-well compound plates, resulting in 50,000 cells/well or 0 cells/well respectively. IFN-γ and LPS were added to the remaining cell suspension at final concentrations of 100 ng/ml and 50 ng/ml respectively, and 50 µL of the stimulated cells were added to all remaining wells on the 384-well compound plates. The plates, with lids, were then placed in a 37° C., 5% $CO_2$ humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 40 µL were added to each plate well. After a twenty minute incubation at room temperature, luminescence was read on an EnVision® Multilabel Reader (PerkinElmer Inc., Waltham, Mass.). For the mass spectrometry assay, 10 µL of supernatant from each well of the compound-treated plates were added to 40 µL of acetonitrile, containing 10 μM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 μL from each well of the acetonitrile extraction plates were added to 90 μL of sterile, distilled $H_2O$ in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as % IDO1 inhibition versus compound concentration following normalization using the formula 100−(100*((U−C2)/(C1−C2))), where U was the unknown value, C1 was the average of the high (100% kynurenine; 0% inhibition) control wells and C2 was the average of the low (0% kynurenine; 100% inhibition) control wells. The data for dose responses in the cytotoxicity assay were plotted as % cytotoxicity versus compound concentration following normalization using the formula 100−(100*((U−C2)/(C1−C2))), where U was the unknown value, C1 was the average of the high (0% cytotoxicity) control wells and C2 was the average of the low (100% cytotoxicity) control wells.

Curve fitting was performed with the equation $y=A+((B-A)/(1+(10^X/10^C)^D))$, where A was the minimum response, B was the maximum response, C was the log ($XC_{50}$) and D was the Hill slope. The results for each test compound were recorded as pIC50 values for the mass spectrometry assay and as pCC50 values for the cytoxicity assay (−C in the above equation).

IDOi MDDC assay: Compounds of the present invention were tested via a high-throughput cellular assay utilizing detection of kynurenine via mass spectrometry. Human monocyte-derived dendritic cells (MDDC) (AllCells®, Alameda, Calif.) were stimulated with human interferon-γ (IFN-γ) (Sigma-Aldrich Corporation, St. Louis, Mo.) and lipopolysaccharide from *Salmonella* minnesota (LPS) (Invivogen, San Diego, Calif.) to induce the expression of indoleamine 2, 3-dioxygenase (IDO1). Compounds with IDO1 inhibitory properties decreased the amount of kynurenine produced by the cells via the tryptophan catabolic pathway.

In preparation for the assay, test compounds were serially diluted 3-fold in DMSO from a typical top concentration of 5 mM and plated at 0.5 μL in 384-well, polystyrene, clear bottom, tissue culture treated plates with lids (Greiner Bio-One, Kremsmünster, Austria) to generate 11-point dose response curves. Low control wells (0% kynurenine) contained 0.5 μL of DMSO in the presence of unstimulated (−IFN-γ/−LPS) MDDCs, and high control wells (100% kynurenine) contained 0.5 μL of DMSO in the presence of stimulated (+IFN-γ/+LPS) MDDCs.

Frozen stocks of MDDCs were washed and recovered in RPMI 1640 medium (Thermo Fisher Scientific, Inc., Waltham, Mass.) supplemented with 10% v/v heat-inactivated fetal bovine serum (FBS) (Thermo Fisher Scientific, Inc., Waltham, Mass.), and 1×penicillin-streptomycin antibiotic solution (Thermo Fisher Scientific, Inc., Waltham, Mass.). The cells were diluted to 1,000,000 cells/mL in the supplemented RPMI 1640 medium. 50 μL of the cell suspension were added to the low control wells, on the previously prepared 384-well compound plates, resulting in 50,000 cells/well. IFN-γ and LPS were added to the remaining cell suspension at final concentrations of 100 ng/ml and 50 ng/ml respectively, and 50 μL of the stimulated cells were added to all remaining wells on the 384-well compound plates. The plates, with lids, were then placed in a 37° C., 5% $CO_2$ humidified incubator for 2 days.

Following incubation, the 384-well plates were removed from the incubator and allowed to equilibrate to room temperature for 30 minutes. 10 μL of supernatant from each well of the compound-treated plates were added to 40 μL of acetonitrile, containing 10 μM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 μL from each well of the acetonitrile extraction plates were added to 90 μL of sterile, distilled $H_2O$ in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as % IDO1 inhibition versus compound concentration following normalization using the formula 100−(100*((U−C2)/(C1−C2))), where U was the unknown value, C1 was the average of the high (100% kynurenine; 0% inhibition) control wells and C2 was the average of the low (0% kynurenine; 100% inhibition) control wells. Curve fitting was performed with the equation)$y=A+((B-A)/(1+(10^X/10^C)^D))$, where A was the minimum response, B was the maximum response, C was the log ($XC_{50}$) and D was the Hill slope. The results for each test compound were recorded as pIC50 values (−C in the above equation).

In vivo pharmacokinetic methods, rat: Male nonfasted Wistar Han rats (n=3) received test article at doses of 1 mg/kg i.v. (1 mL/kg) and 5 mg/kg p.o. (5 ml/kg) formulated in a DMSO/solutol/10% hydroxyl-propyl β cyclodextrin (10:10:80) dosing vehicle. For all animals, food and water was provided ad libitum. Blood samples were withdrawn from a surgically-implanted venous cannula at timed intervals for 24 h after dose administration, treated with EDTA, and centrifuged to harvest plasma for LC/MS/MS analysis. Plasma concentration-time data for individual rats were analyzed by noncompartmental analysis using the Phoenix™ WinNonlin® (version 6.2.1, Pharsight Corp., St. Louis, Mo.) software to generate pharmacokinetic parameter estimates.

Although the invention has been shown and described above with reference to some embodiments, those skilled in the art will readily appreciate that the specific experiments detailed are only illustrative of the invention. It should be understood that various modifications can be made without departing from the spirit of the invention.

For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims. Accordingly, the invention is limited only by the following claims. All publications, issued patents, patent applications, books and journal articles, cited in this application are each herein incorporated by reference in their entirety.

REFERENCES

Lohse N, Hansen A B, Pedersen G, Kronborg G, Gerstoft J, Sørensen H T, Vaeth M, Obel N. Survival of persons with and without HIV infection in Denmark, 1995-2005. Ann Intern Med. 2007 Jan. 16;146(2):87-95.

Deeks S G. HIV infection, inflammation, immunosenescence, and aging. Annu Rev Med. 2011;62:141-55.

Hunt P W, Sinclair E, Rodriguez B, Shive C, Clagett B, Funderburg N, Robinson J, Huang Y, Epling L, Martin J N, Deeks S G, Meinert C L, Van Natta M L, Jabs D A, Lederman M M. Gut epithelial barrier dysfunction and innate immune activation predict mortality in treated HIV infection. J Infect Dis. 2014 Oct, 15; 210(8):1228-38.

Tenorio A R, Zheng Y, Bosch R J, Krishnan S, Rodriguez B, Hunt P W, Plants J, Seth A, Wilson C C, Deeks S G, Lederman M M, Landay A L. Soluble markers of inflammation and coagulation but not T-cell activation predict non-AIDS-defining morbid events during suppressive antiretroviral treatment. J Infect Dis. 2014 Oct. 15; 210 (8):1248-59.

Byakwaga H, Boum Y 2nd, Huang Y, Muzoora C, Kembabazi A, Weiser S D, Bennett J, Cao H, Haberer J E, Deeks S G, Bangsberg D R, McCune J M, Martin J N, Hunt P W. The kynurenine pathway of tryptophan catabolism, CD4+ T-cell recovery, and mortality among HIV-infected Ugandans initiating antiretroviral therapy. J Infect Dis. 2014 Aug. 1; 210(3):383-91.

Pearson J T, Siu S, Meininger D P, Wienkers L C, Rock D A. In vitro modulation of cytochrome P450 reductase supportedindoleamine 2,3-dioxygenase activity by allosteric effectors cytochrome b(5) and methylene blue. Biochemistry 49, 2647-2656 (2010)

What is claimed is:

1. A compound having the structure of Formula (I):

or pharmaceutically acceptable salt, thereof, wherein:
X is $CH_2$ or C(O);
$R^1$ is —$NR^2R^3$;
$R^2$ is —H or —$CH_3$;
$R^3$ is selected from the group consisting of:

2. A compound or salt according to claim 1 having the structure of Formula (II):

or pharmaceutically acceptable salt, thereof.

3. A compound or salt according to claim 1 having the structure of Formula (III):

or pharmaceutically acceptable salt, thereof.

4. A compound or salt according to claim 1 having the structure of Formula (IV):

or pharmaceutically acceptable salt, thereof.

5. A compound or salt according to claim 1 having the structure of Formula (V):

or pharmaceutically acceptable salt, thereof.

6. A compound or salt according to claim 1 having the structure of Formula (VI):

(VI)
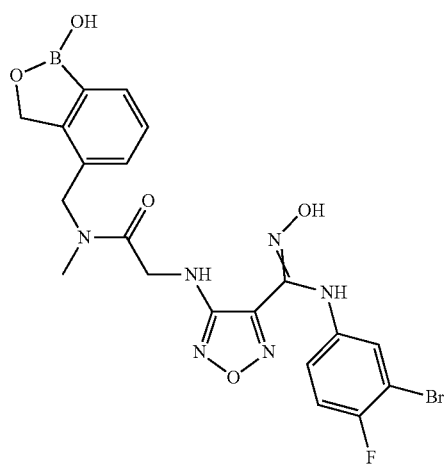
or pharmaceutically acceptable salt, thereof.
7. A compound or salt according to claim 1 having the structure of Formula (VII):
(VII)
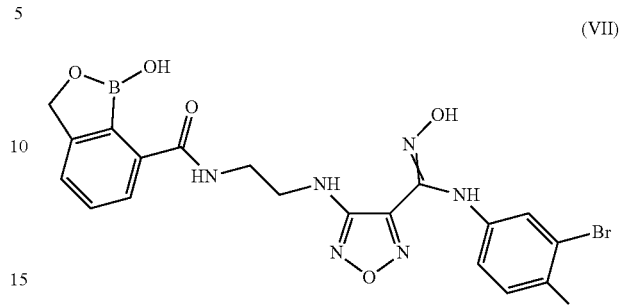
or pharmaceutically acceptable salt, thereof.
* * * * *